US009205046B2

(12) United States Patent
Shoichet et al.

(10) Patent No.: US 9,205,046 B2
(45) Date of Patent: *Dec. 8, 2015

(54) ENHANCED STABILITY OF INVERSE THERMAL GELLING COMPOSITE HYDROGELS

(75) Inventors: Molly S. Shoichet, Toronto (CA); M. Douglas Baumann, St. Catharines (CA); Catherine Elizabeth Kang, Chicago, IL (US)

(73) Assignee: The Governing Council of the University of Toronto, Toronto, Ontario (CA)

( * ) Notice: Subject to any disclaimer, the term of this patent is extended or adjusted under 35 U.S.C. 154(b) by 128 days.

This patent is subject to a terminal disclaimer.

(21) Appl. No.: 12/778,879

(22) Filed: May 12, 2010

(65) Prior Publication Data
US 2010/0285113 A1 Nov. 11, 2010

Related U.S. Application Data

(63) Continuation-in-part of application No. 11/410,831, filed on Apr. 25, 2006, now Pat. No. 7,767,656.

(60) Provisional application No. 60/674,299, filed on Apr. 25, 2005.

(51) Int. Cl.
*A61K 31/717* (2006.01)
*A61K 9/10* (2006.01)
*A61K 9/127* (2006.01)
*A61P 25/00* (2006.01)
*A61P 41/00* (2006.01)
*A61K 9/00* (2006.01)
*A61K 38/18* (2006.01)
*A61K 47/36* (2006.01)
*A61K 47/38* (2006.01)

(52) U.S. Cl.
CPC ............ *A61K 9/0024* (2013.01); *A61K 9/0095* (2013.01); *A61K 38/1825* (2013.01); *A61K 38/1858* (2013.01); *A61K 38/1866* (2013.01); *A61K 38/1891* (2013.01); *A61K 47/36* (2013.01); *A61K 47/38* (2013.01)

(58) Field of Classification Search
CPC ............ A61K 9/0024; A61K 9/0095; A61K 38/1825; A61K 38/1891; A61K 38/1866; A61K 38/1858; A61K 47/36; A61K 47/38
USPC .................. 424/450, 486, 487, 488; 426/573; 514/44 A, 44 R, 9.6; 977/773, 788
See application file for complete search history.

(56) References Cited

U.S. PATENT DOCUMENTS 5,942,253 A * 8/1999 Gombotz et al. ............. 424/501
6,462,093 B1 * 10/2002 Miyamoto et al. ......... 514/772.3
7,767,656 B2 8/2010 Shoichet et al.
2005/0119219 A1 * 6/2005 Bellini et al. ................... 514/54
2006/0002852 A1 * 1/2006 Saltzman et al. ............ 424/1.11
2006/0280797 A1 * 12/2006 Shoichet et al. ............. 424/486
2009/0220497 A1 * 9/2009 Brown et al. ............. 424/133.1

FOREIGN PATENT DOCUMENTS

IN   WO 2008041245   *   4/2008   ............... A61K 9/16

OTHER PUBLICATIONS

Nindl et al. Exerc Sport Sci Rev. 2003, 31(4), 161-6; Abstract; 1 page.*
Bikfalvi, A., et al., Biological roles of fibroblast growth factor-2. Endocr Rev, 1997. 18(1): p. 26-45.
Bracken, M.B., et al., Methylprednisolone or naloxone treatment after acute spinal cord injury: 1-year follow-up data. Results of the second National Acute Spinal Cord Injury Study. J Neurosurg, 1992. 76(1): p. 23-31.
Campoccia, D. et al. Semisynthetic resorbable materials from hyaluronan esterification, Fidia Advanced Biopolymers, Albano Terme (PD), Italy. Biomaterials. Dec. 1998;19(23):2101-27.
Chvatal, S.A., et al., Spatial distribution and acute anti-inflammatory effects of Methylprednisolone after sustained local delivery to the contused spinal cord. Biomaterials, 2008. 29(12): p. 1967-75.
Cruise, G.M., D.S. Scharp, and J.A. Hubbell, Characterization of permeability and network structure of interfacially photopolymerized poly(ethylene glycol) diacrylate hydrogels. Biomaterials, 1998. 19(14): p. 1287-94.
Cui, F.Z., et al. Hyaluronic acid hydrogel immobilized with RGD peptides for brain tissue engineering. J. Mater. Sci. Mater.Med. Dec. 2006;17(12):1393-401.
Dunne, M., I. Corrigan, and Z. Ramtoola, Influence of particle size and dissolution conditions on the degradation properties of polylactide-co-glycolide particles. Biomaterials, 2000. 21(16): p. 1659-68.

(Continued)

*Primary Examiner* — Anoop Singh
*Assistant Examiner* — Doan Phan
(74) *Attorney, Agent, or Firm* — Price Heneveld LLP

(57) ABSTRACT

The present invention relates to a composite hydrogel comprising a blend of an aqueous solution of an anionic polysaccharide or a derivative thereof, such as hyaluronan (also commonly referred to as hyaluronic acid) or a derivative thereof and an aqueous solution of methylcellulose or another water soluble cellulose derivative thereof, having dispersed polymeric particles, such as polymeric hydrophobic particles therein selected from micro particles and nanoparticles, and wherein the stability of the hydrogel is enhanced relative to the stability of the hydrogel alone. The polymeric particles may contain at least one therapeutic agent, in which case each therapeutic agent exhibits a linear sustained release rate that can be tuned or altered by selecting the appropriate polymer formulation of the micro particles and/or nanoparticles. The composite may be injectable, and in the absence of a therapeutic agent may be used as a bulking agent for reconstructive and cosmetic surgery or may act as a platform for subsequent delivery of therapeutic agents.

13 Claims, 8 Drawing Sheets

(56) References Cited

OTHER PUBLICATIONS

Duval et al. Synthesis and characterization of some covalent Dextran-Polyoxyethyleneglycol Derivatives in Carbohydrate Polymers, 15, (1991), 233-242.

Fehlings, Michael G., et al., An evidence-based review of decompressive surgery in acute spinal cord injury: rationale, indications, and timing based on experimental and clinical studies, J. Neurosurg (Spine 1) 91:1-11, 1999.

Gerdin, B. and R. Hallgren, Dynamic role of hyaluronan (HYA) in connective tissue activation and inflammation. Journal of Internal Medicine, 1997. 242(1): p. 49-55.

Gianolio, DA., et al Hyaluronan tethered opioid depots: synthetic strategies and release kinetics in vitro and in vivo. Bioconjugate Chem. Sep. 2008;19(9):1767-74.

Gupta, D., C.H. Tator, and M.S. Shoichet, Fast-gelling injectable blend of hyaluronan and methylcellulose for intrathecal, localized delivery to the injured spinal cord. Biomaterials, 2006. 27(11): p. 2370-9.

Han, J.H., et al., Lactitol-based poly(ether polyol) hydrogels for controlled release chemical and drug delivery systems. Journal of Agricultural and Food Chemistry, 2000. 48(11): p. 5278-5282.

Hannila, S.S. and M.T. Filbin, The role of cyclic AMP signaling in promoting axonal regeneration after spinal cord injury. Exp Neurol, 2008. 209(2): p. 321-32.

Hennink, W.E., et al., Controlled release of proteins from dextran hydrogels. Journal of Controlled Release, 1996. 39(1): p. 47-55.

Jiang, D., et al., Hyaluronan in Tissue Injury and Repair, Annu. Rev. Cell Dev. Biol. 2007, 23:435-61.

Hamann, Jimenez., M.C., C.H. Tator, and M.S. Shoichet, Injectable intrathecal delivery system for localized administration of EGF and FGF-2 to the injured rat spinal cord. Exp Neurol, 2005. 194(1): p. 106-19.

Jones, L.L. and M.H. Tuszynski, Chronic intrathecal infusions after spinal cord injury cause scarring and compression. Microscopy Research and Technique, 2001. 54(5): p. 317-324.

Kang, C.E., et al., A New Paradigm for Local and Sustained Release of Therapeutic Molecules to the Injured Spinal Cord for Neuroprotection and Tissue Repair. Tissue Eng Part A, 2009, pp. 595-604.

Kitchens, D.L., E.Y. Snyder, and D.I. Gottlieb, FGF and EGF are mitogens for immortalized neural progenitors. J Neurobiol, 1994. 25(7): p. 797-807.

Krewson, C.E., M.L. Klaman, and W.M. Saltzman, Distribution of nerve growth factor following direct delivery to brain interstitium. Brain Res, 1995. 680(1-2): p. 196-206.

Lee, T.T., et al., Neuroprotective effects of basic fibroblast growth factor following spinal cord contusion injury in the rat. J Neurotrauma, 1999. 16(5): p. 347-56; 13.

Li, Y., et al., Effects of the AMPA receptor antagonist NBQX on the development and expression of behavioral sensitization to cocaine and amphetamine. Psychopharmacology (Berl), 1997. 134(3): p. 266-76.

Lin, C.C. and A.T. Metters, Hydrogels in controlled release formulations: network design and mathematical modeling. Adv Drug Deliv Rev, 2006. 58(12-13): p. 1379-408.

Loy, D.N., et al., Temporal progression of angiogenesis and basal lamina deposition after contusive spinal cord injury in the adult rat. J Comp Neurol, 2002. 445(4): p. 308-24.

Mackay, M.E., et al., General strategies for nanoparticle dispersion. Science, 2006. 311(5768): p. 1740-3.

Mckerracher, L. and H. Higuchi, Targeting Rho to stimulate repair after spinal cord injury. J Neurotrauma, 2006. 23(3-4): p. 309-17.

Miller, S.M., Methylprednisolone in acute spinal cord injury: a tarnished standard. J Neurosurg Anesthesiol, 2008. 20 (2): p. 140-2.

Peppas, N. A. and E.W. Merrill, Polyvinyl-Alcohol) Hydrogels—Reinforcement of Radiation-Crosslinked Networks by Crystallization. Journal of Polymer Science Part a-Polymer Chemistry, 1976. 14(2): p. 441-457.

N. A. Peppas, C.T. Reinhart, Solute diffusion in swollen membranes. 1. A new theory, J. Membr. Sci. 15 (3) (1983) 275-287.

Ramer, L.M., M.S. Raner, and J.D. Steeves, Setting the stage for functional repair of spinal cord injuries: a cast of thousands. Spinal Cord, 2005. 43(3): p. 134-61.

Romero, M.I., et al., Functional regeneration of chronically injured sensory afferents into adult spinal cord after neurotrophin gene therapy. J Neurosci, 2001. 21(21): p. 8408-16.

Rozet, I., Methylprednisolone in acute spinal cord injury: is there any other ethical choice? J Neurosurg Anesthesiol, 2008. 20(2): p. 137-9.

Saunders, F.L., Adsorption of Methylcellulose on Polystyrene Latexes. Journal of Colloid and Interface Science, 1968. 28(3-4): p. 475-80.

Schupper, N., Y. Rabin, and M. Rosenbluh, Multiple stages in the aging of a physical polymer gel. Macromolecules, 2008. 41(11): p. 3983-3994.

Schwab, M.E., Nogo and axon regeneration. Curr Opin Neurobiol, 2004. 14(1): p. 118-24.

Scriabine, A., T. Schuurman, and J. Traber, Pharmacological basis for the use of nimodipine in central nervous system disorders. Faseb J, 1989. 3(7): p. 1799-806.

Sinha, V.R. and A. Trehan, Biodegradable microspheres for protein delivery. Journal of Controlled Release, 2003. 90(3): p. 261-280.

Soppimath, KS., et al., Biodegradable polymeric nanoparticles as drug delivery devices. J Control Release, 2001. 70(1-2): p. 1-20.

Tator, Charles H.; Current use and timing of spinal surgery for management of acute spinal cord injury in North America: results of a retrospective multicenter study; J. Neurosurg (Spine 1) 91:12-18 (1999).

Tator, C.H.; Strategies for recovery and regeneration after brain and spinal cord injury; Inj Prey 2002 9: iv33-iv36.

Teng, Y.D., et al., Basic fibroblast growth factor increases long-term survival of spinal motor neurons and improves respiratory function after experimental spinal cord injury. J Neurosci, 1999. 19(16): p. 7037-47.

Terada, H., et al., Reduction of ischemic spinal cord injury by dextrorphan: comparison of several methods of administration. J Thorac Cardiovasc Surg, 2001. 122(5): p. 979-85.

Tobias, C.A., et al., Delayed grafting of BDNF and NT-3 producing fibroblasts into the injured spinal cord stimulates sprouting, partially rescues axotomized red nucleus neurons from loss and atrophy, and provides limited regeneration. Exp Neurol, 2003. 184(1): p. 97-113.

Uchida, K., et al., Progressive changes in neurofilament proteins and growth-associated protein-43 immunoreactivities at the site of cervical spinal cord compression in spinal hyperostotic mice. Spine, 2002. 27(5): p. 480-6.

Wong, H.M., Wang, J.J., and Wang, C, In Vitro Sustained Release of Human Immunoglobulin G from Biodegradable Microspheres. Ind. Eng. Chem. Res., 2001. 40: p. 933-948.

Xu, Y. et al., Salt-Assisted and Salt-Suppressed Sol-Gel Transitions of Methylcellulose in Water, Langmuir 2004, 20-646-652.

Yaksh, T.L., et al., Intrathecal ketorolac in dogs and rats. Toxicol Sci, 2004. 80(2): p. 322-34.

Ying, L., et al., In vitro evaluation of lysozyme-loaded microspheres in thermosensitive methylcellulose-based hydrogel. Chinese Journal of Chemical Engineering, 2007. 15(4): p. 566-572.

Liu, X., K. Nakamura, and A.M. Lowman, Composite hydrogels for sustained release of therapeutic agents. Soft Materials, 2003. 1(3): p. 393-408.

C. Basilico and D. Moscatelli, The FGF family of growth factors and oncogenes, Adv Cancer Res. 59 (1992) 115-65.

Baumann, M.D., C.E. Kang, J.C. Stanwick, Y. Wang, H. Kim, Y. Lapitsky, and M.S. Shoichet, An injectable drug delivery platform for sustained combination therapy, J Control Release. (2009) pp. 205-213.

Chenite, A. et al. Novel injectable neutral solutions of chitosan form biodegradable gels in situ (Biomaterials 21:2155-2161, 2000.

Cho, K.Y. et al.; Release of ciprofloxacin from poloxamer-graft-hyaluronic acid hydrogels in vitro; International Journal of Pharmaceutics (2003) 260:83-91.

Crank; Methods of solution when the diffusion coefficient is constant, p. 11-12 (1956).

Hoffman, A.S. et al. Bioconjugates fo Intelligent Polymers and Recognition Proteins for Use in Diagnostics and Affinity Separations; Clinical Chemistry 46(9):1478-1486 (2000).

(56) References Cited

OTHER PUBLICATIONS

Hooper, J.B. and K.S. Schweizer, Contact Aggregation, Bridging, and Steric Stabilization in Dense Polymer-Particle Particle Mixtures. Macromolecules, 2005. 38: p. 8858-8869.

Hooper, J.B. and K.S. Schweizer, Theory of phase separation in polymer nanocomposites. Macromolecules, 2006. 39(15): p. 5133-5142.

Kang, C.E.; Tator, C.H.; Shoichet, M.S. Poly(ethylene glycol) Modification Enhances Penetration of Fibroblast Growth Factor 2 to Spinal Cord Tissue from an Intrathecal Delivery System; Journal of Controlled Release 144 (2010) 25-31.

Katre, N. V.; The conjugation of proteins with polyethylene glycol and other polymers. Adv. Drug Delivery Reviews, 10, 91-114 (1993).

Kim, M.R. et al.; Temperature-responsive and degradable hyaluronic acid/Pluronic composite hydrogels for controlled release of human growth hormone; J. Controlled Release 80: 69-77 (2002).

I. Koyanagi, C.H. Tator, and P.J. Lea, Three-dimensional analysis of the vascular system in the rat spinal cord with scanning electron microscopy of vascular corrosion casts. Part 2: Acute spinal cord injury, Neurosurgery. 33(2) (1993) 285-91; discussion 292.

I. Koyanagi, C.H. Tator, and P.J. Lea, Three-dimensional analysis of the vascular system in the rat spinal cord with scanning electron microscopy of vascular corrosion casts. Part 1: Normal spinal cord, Neurosurgery. 33 (1993) 277-83; discussion 283-4.

Liang, H. et al. Novel Method using a temperature-sensitive polymer (methylcellulose) to thermally gel aqueous alginate as a pH-sensitive hydrogel; Biomacromolecules 5:1917-1925 (2004).

R. Montesano, J.D. Vassalli, A. Baird, R. Guillemin, and L. Orci, Basic fibroblast growth factor induces angiogenesis in vitro, Proc Natl Acad Sci U S A. 83 (1986) 7297-301.

Nucci, M.L. et al., The therapeutic value of poly(ethyleen glycol)-modified proteins; Advances in Drug Delivery Review, 6, (1991),133-151.

Ohya, S. et al.; Thermoresponsive artificial extracellular matrix for tissue engineering: Hyaluronic acid bioconjugated with ploy(N-isopropylacrylamide) Grafts; Biomacromolecules (2001) 2:856-863.

M. Relf, S. Lejeune, P.A. Scott, S. Fox, K. Smith, R. Leek, A. Moghaddam, R. Whitehouse, R. Bicknelli, and A.L. Harris, Expression of the angiogenic factors vascular endothelial cell growth factor, acidic and basic fibroblast growth factor, tumor growth factor beta-1, platelet-derived endothelial cell growth factor, placenta growth factor, and pleiotrophin in human primary breast cancer and its relation to angiogenesis, Cancer Res. 57 (1997).

Ritger, P.L. and N. A. Peppas, A Simple Equation for Description of Solute Release 1. Fickian and Non-Fickian Release from Non-Swellable Devices in the Form of Slabs, Spheres, Cylinders or Discs. Journal of Controlled Release, 1987. 5: p. 23-36.

Ritger, P.L. and N. A. Peppas, A Simple Equation for Description of Solute Release 2. Fickian and Anomalous Release from Swellable Devices. Journal of Controlled Release, 1987. 5: p. 37-42.

A.S. Rivlin and C.H. Tator, Effect of duration of acute spinal cord compression in a new acute cord injury model in the rat, Surg Neurol. 10 (1978) 39-43.

Tate, M.C. et al., Biocompatability of methylcellulose-based constructions designed for intracerebral gelation following experimental traumatic brain injury. Biomaterials (2001) 22:1113-1123.

Wosnick, J., Baumann, M.D., Shoichett, M.S., Tissue Therapy in the Central Nervous System; pp. 2-24 in Principles of Regenerative Medicine, A. Atala, Lanza, R., Thomson, J.A., Nerem, R.M., eds., Editor. 2007, Elsevier: New York.

Schexnailder, P. and G. Schmidt, Nanocomposite polymer hydrogels. Colloid and Polymer Science, 2009. 287(1): p. 1-11.

Y. Shing, J. Folkman, C. Haudenschild, D. Lund, R. Crum, and M. Klagsbrun, Angiogenesis is stimulated by a tumor-derived endothelial cell growth factor, Journal of Cellular Biochemistry. 29 (1985) 275-87.

Silver, F.H. et al., Physical Properties of Hyaluronic Acid and Hydroxypropylmethylcellulose in Solution: Evaluation of coating ability; Journal of Applied Biomaterials (1994) 5:89-98.

U.S. Appl. No. 12/785,083, filed May 21, 2010, to Shoichet et al.

* cited by examiner

ENHANCED STABILITY OF INVERSE THERMAL GELLING COMPOSITE HYDROGELS

CROSS REFERENCE TO RELATED APPLICATIONS

This application is a continuation in part of U.S. patent application Ser. No. 11/410,831, filed Apr. 25, 2006, now U.S. Pat. No. 7,767,656 which application claims benefit to U.S. Provisional Application Ser. No. 60/674,299, filed Apr. 25, 2005, both of which are incorporated herein by reference in their entirety

FIELD OF THE INVENTION

The present invention relates to a composite hydrogel comprising a blend of an aqueous solution of an anionic polysaccharide or a derivative thereof, such as hyaluronan (also commonly referred to as hyaluronic acid) or a derivative thereof and an aqueous solution of methylcellulose or another water soluble cellulose derivative thereof, having dispersed polymeric particles, such as polymeric hydrophobic particles therein selected from micro particles and nanoparticles, and wherein the stability of the hydrogel is enhanced relative to the stability of the hydrogel alone. The polymeric particles may contain at least one therapeutic agent, in which case each therapeutic agent exhibits a linear sustained release rate that can be tuned or altered by selecting the appropriate polymer formulation of the micro particles and/or nanoparticles. The composite may be injectable, and in the absence of a therapeutic agent may be used as a bulking agent for reconstructive and cosmetic surgery or may act as a platform for subsequent delivery of therapeutic agents.

BACKGROUND OF THE INVENTION

About 11,000 new cases of traumatic spinal cord injury (SCI) are reported in the United States annually, primarily affecting young adults [Wosnick, J., Baumann, M. D., Shoichet, M. S., *Tissue Therapy in the Central Nervous System*, in *Principles of Regenerative Medicine*, A. Atala, Lanza, R., Thomson, J. A., Nerem, R. M., eds., Editor. 2007, Elsevier: New York]. A majority of these cases are compression injuries wherein the cord is bruised under displacement of the spinal column, resulting in formation of a cystic cavity in the days after injury. As tissue degenerates, the degree of paralysis increases, causing further permanent loss of motor control and sensory perception. For this reason compression injuries are normally described as occurring in two stages, the immediate primary injury and subsequent secondary injury. Various treatment strategies are being developed with a view of limiting degeneration after the primary injury and/or promoting regeneration after secondary injury. Currently, however, there is no standard clinical treatment, other than application of methylprednisolone, the efficacy of which is still debated [Miller, S. M., *Methylprednisolone in acute spinal cord injury: a tarnished standard*. J Neurosurg Anesthesiol, 2008. 20(2): p. 140-2; Rozet, I., *Methylprednisolone in acute spinal cord injury: is there any other ethical choice?* J Neurosurg Anesthesiol, 2008. 20(2): p. 137-9]. Similarly, there is no standard of care for traumatic brain injury or stroke. For example, there is no cure for stroke, and the only FDA approved treatment is tissue plasminogen activator (tPA), a thrombolytic agent with limited therapeutic benefit [*Stroke and cerebrovascular accidents*. World Health Organization, Circulation, 2009].

Therapies designed to enhance cell survival during the trauma of secondary injury are focused on the hours to days following the primary injury and seek to limit vascular damage, excitotoxicity, and the inflammatory response around the injury site [Ramer, L. M., M. S. Ramer, and J. D. Steeves, *Setting the stage for functional repair of spinal cord injuries: a cast of thousands*. Spinal Cord, 2005. 43(3): p. 134-61.]. Neuroprotective strategies target one or more of these mechanisms with the goal of minimizing the death of motor and sensory neurons. For example, methylprednisolone targets acute inflammation and inhibits lipid peroxidation [Bracken, M. B., et al., *Methylprednisolone or naloxone treatment after acute spinal cord injury: 1-year follow-up data. Results of the second National Acute Spinal Cord Injury Study*. J Neurosurg, 1992. 76(1): p. 23-31], while the sodium channel antagonist NBQX minimizes excitotoxicity [Li, Y., et al., *Effects of the AMPA receptor antagonist NBQX on the development and expression of behavioral sensitization to cocaine and amphetamine*. Psychopharmacology (Berl), 1997. 134 (3): p. 266-76] and nimodipine limits vasospasm [Scriabine, A., T. Schuurman, and J. Traber, *Pharmacological basis for the use of nimodipine in central nervous system disorders*. Faseb J, 1989. 3(7): p. 1799-806].

Neuroregenerative therapies enhance axonal outgrowth by either direct action or suppression of the inhibitory environment after injury. For example, numerous neurotrophins stimulate proliferation and regeneration, including: nerve growth factor [Romero, M. I., et al., *Functional regeneration of chronically injured sensory afferents into adult spinal cord after neurotrophin gene therapy*. J Neurosci, 2001. 21(21): p. 8408-16], brain derived neurotrophic factor [Tobias, C. A., et al., *Delayed grafting of BDNF and NT-3 producing fibroblasts into the injured spinal cord stimulates sprouting, partially rescues axotomized red nucleus neurons from loss and atrophy, and provides limited regeneration*. Exp Neurol, 2003. 184(1): p. 97-113], epidermal growth factor (EGF) [Kitchens, D. L., E. Y. Snyder, and D. I. Gottlieb, *FGF and EGF are mitogens for immortalized neural progenitors*. J Neurobiol, 1994. 25(7): p. 797-807] and basic fibroblast growth factor (FGF-2) [Bikfalvi, A., et al., *Biological roles of fibroblast growth factor-2*. Endocr Rev, 1997. 18(1): p. 26-45]. FGF-2 has also been reported to prevent neuronal cell death [Lee, T. T., et al., *Neuroprotective effects of basic fibroblast growth factor following spinal cord contusion injury in the rat*. J Neurotrauma, 1999. 16(5): p. 347-56; 13; Teng, Y. D., et al., *Basic fibroblast growth factor increases long-term survival of spinal motor neurons and improves respiratory function after experimental spinal cord injury*. J Neurosci, 1999. 19(16): p. 7037-47] and promote angiogenesis [Loy, D. N., et al., *Temporal progression of angiogenesis and basal lamina deposition after contusive spinal cord injury in the adult rat*. J Comp Neurol, 2002. 445(4): p. 308-24]. The family of antibodies targeting NogoA [Schwab, M. E., *Nogo and axon regeneration*. Curr Opin Neurobiol, 2004. 14(1): p. 118-24], rho kinase inhibitors [McKerracher, L. and H. Higuchi, *Targeting Rho to stimulate repair after spinal cord injury*. J Neurotrauma, 2006. 23(3-4): p. 309-17] and cyclic AMP [Hannila, S. S. and M. T. Filbin, *The role of cyclic AMP signaling in promoting axonal regeneration after spinal cord injury*. Exp Neurol, 2008. 209(2): p. 321-32] are well known anti-inhibitory molecules that act by blocking or overriding the inhibitory environment present post-injury. Similarly, chondroitinase abc requires local delivery as it cannot cross the blood-spinal cord barrier (or the blood-brain barrier) and requires sustained delivery, which is not easily obtained by other delivery methods. Chondroitinase abc acts to degrade the chondroitin sulfate proteoglycan present in the injured central nervous system and thereby facilitates axonal regeneration. These molecules are often delivered for extended periods, ranging from 7-28 days.

Whether neuroprotective or neuroregenerative, delivery is limited to local strategies as most molecules are unable to cross the blood-spinal cord barrier and blood-brain barrier, confounding systemic delivery. Current local delivery strategies are inadequate: bolus delivery often results in rapid clearance due to cerebrospinal fluid flow in the intrathecal space [Terada, H., et al., *Reduction of ischemic spinal cord injury by dextrorphan: comparison of several methods of administration*. J Thorac Cardiovasc Surg, 2001. 122(5): p. 979-85; 19; Yaksh, T. L., et al., *Intrathecal ketorolac in dogs and rats*. Toxicol Sci, 2004. 80(2): p. 322-34], whereas the indwelling catheter/external pump is associated with scarring and infection [Jones, L. L. and M. H. Tuszynski, *Chronic intrathecal infusions after spinal cord injury cause scarring and compression*. Microscopy Research and Technique, 2001. 54(5): p. 317-324]. With a view toward developing a minimally-invasive drug delivery system that would provide sustained, local release of factors, a delivery paradigm is presented in which a drug loaded thermo-sensitive hydrogel is injected intrathecally and remains localized at the site of injection, delivering the drug load to the cerebral spinal fluid (CSF) with concomitant access to the brain and spinal cord [Jimenez Hamann, M. C., et al., *Novel intrathecal delivery system for treatment of spinal cord injury*. Exp Neurol, 2003. 182(2): p. 300-9] and then biodegrading, has been described. In this manner the hydrogel provides a platform for localized release over the life of the material. Evidence shows that intrathecal injection bypasses the dura and arachnoid mater and limits convective drug redistribution from CSF flow, all barriers that negatively impact epidural delivery [Chvatal, S. A., et al., *Spatial distribution and acute anti-inflammatory effects of Methylprednisolone after sustained local delivery to the contused spinal cord*. Biomaterials, 2008. 29(12): p. 1967-75]. Subsequently, a biocompatible and biodegradable blend of 2 wt % hyaluronan and 7 wt % methylcellulose (2:7 HAMC) has been developed for this application [Gupta, D., C. H. Tator, and M. S. Shoichet, *Fast-gelling injectable blend of hyaluronan and methylcellulose for intrathecal, localized delivery to the injured spinal cord*. Biomaterials, 2006. 27(11): p. 2370-9]. The role of MC is to form a physical hydrogel through hydrophobic junctions [Schupper, N., Y. Rabin, and M. Rosenbluh, *Multiple stages in the aging of a physical polymer gel*. Macromolecules, 2008. 41(11): p. 3983-3994] and HA to increase solution viscosity and to enhance MC gel strength at lower temperatures through the salting out effect. 2:7 HAMC was found to degrade within 4-7 days in vivo, making it well suited for neuroprotective delivery strategies but unsuitable for drug delivery over the 2-4 weeks necessary for regenerative strategies [Kang, C. E., et al., *A New Paradigm for Local and Sustained Release of Therapeutic Molecules to the Injured Spinal Cord for Neuroprotection and Tissue Repair*. Tissue Eng Part A, 2008]. Accordingly, these injectable hydrogels were used to deliver erythropoietin [Kang, C. E., et al., *A New Paradigm for Local and Sustained Release of Therapeutic Molecules to the Injured Spinal Cord for Neuroprotection and Tissue Repair*. Tissue Eng Part A, 2008], as well as EGF and FGF-2 via simple diffusion [Jimenez Hamann, M. C., C. H. Tator, and M. S. Shoichet, *Injectable intrathecal delivery system for localized administration of EGF and FGF-2 to the injured rat spinal cord*. Exp Neurol, 2005. 194(1): p. 106-19]. For soluble molecules, the release profile is determined principally by diffusivity and occurs within 24 hours due to the short diffusive path length in vivo [Jimenez Hamann, M. C., C. H. Tator, and M. S. Shoichet, *Injectable intrathecal delivery system for localized administration of EGF and FGF-2 to the injured rat spinal cord*. Exp Neurol, 2005. 194(1): p. 106-19; Kang, C. E.; Tator, C. H.; Shoichet, M. S. 2010. *Poly(ethylene glycol) Modification Enhances Penetration of Fibroblast Growth Factor 2 to Spinal Cord Tissue from an Intrathecal Delivery System* J. Control Release; doi: 10.1016/j.jconrel.2010.01.029].

As mentioned above, U.S. parent patent application Ser. No. 11/410,831 describes a polymer matrix comprising an inverse thermal gelling polymer and an anionic polymer, for example HAMC that exists as a solid gel. This polymer matrix has a faster gelling rate than the inverse gelling polymer, and may be used alone or as a drug delivery vehicle for many applications. In particular, the polymer matrix can be used for localized, targeted delivery of pharmaceutical agents upon injection providing sustained release. A particular use of this invention is in delivery of a therapeutic agent to a fluid-filled space, such as the intrathecal space, in a highly localized, targeted manner, wherein the polymer matrix-contained therapeutic agent is able to circumvent the blood-spinal cord barrier or blood-brain barrier and enter the target tissue directly.

U.S. Pat. No. 6,335,035 ('035) to Drizen, et al. is a divisional of U.S. Pat. No. 6,063,405 to Drizen et al. which teaches sustained release compositions comprising a drug dispersed within a polymer matrix, methods of producing the same and treatments with the complex. The '035 patent discloses a sustained drug delivery system, which comprises a drug dispersed within a polymer matrix solubilized or suspended in a polymer matrix. The polymer matrix is composed of a highly negatively charged polymer material selected from the group consisting of polysulfated glucosoglycans, glycoaminoglycans, mucopolysaccharides and mixtures thereof, and a nonionic polymer selected from the group consisting of carboxymethylcellulose sodium, hydroxypropylcellulose and mixtures thereof. Nonionic polymers are generally used in amounts of 0.1% to 1.0% and preferably from 0.5% to 1.0%. Nonionic polymers in amounts above 1.0% are not used as they result in the formation of a solid gel product when employed in combination with an anionic polymer.

U.S. Pat. No. 6,692,766 to Rubinstein et al. concerns a controlled release drug delivery system comprising a drug which is susceptible to enzymatic degradation by enzymes present in the intestinal tract; and a polymeric matrix which undergoes erosion in the gastrointestinal tract comprising a hydrogel-forming polymer selected from the group consisting of (a) polymers which are themselves capable of enhancing absorption of said drug across the intestinal mucosal tissues and of inhibiting degradation of said drug by intestinal enzymes; and (b) polymers which are not themselves capable of enhancing absorption of said drug across the intestinal mucosal tissues and of inhibiting degradation of said drug by intestinal enzymes.

U.S. Pat. No. 6,716,251 to Asius et al. discloses an injection implant for filling up wrinkles, thin lines, skin cracks and scars for reparative or plastic surgery, aesthetic dermatology and for filling up gums in dental treatment. The invention concerns the use of biologically absorbable polymer microspheres or micro particles suspended in a gel.

U.S. Pat. No. 6,586,493 to Massia et al. discloses hyaluronate-containing hydrogels having angiogenic and vascularizing activity and pre-gel blends for preparing the hydrogels. The hydrogels contain a cross-linked matrix of a non-angiogenic hyaluronate and a derivatized polysaccharide material, in which cross-linking is effected by free-radical polymerization.

JP2003-342197 discloses a heat gelling pharmaceutical preparation containing methylcellulose and hyaluronic acid that is liquid at room temperature and gels upon administration to the eye.

The literature also teaches the properties of polymer matrices and their use as drug delivery vehicles (Xu et al. Langmuir, (2004) 20(3): 646-652, Liang et al. Biomacromolecules, 2004. 5(5):1917-25, Ohya et al. Biomacromolecules (2001) 2:856-863, Cho et al. International Journal of Pharmaceutics (2003) 260:83-91, Kim et al. Journal of Controlled Release (2002) 80:69-77, Tate et al. Biomaterials (2001) 22:1113-1123, and Silver et al., Journal of Applied Biomaterials (1994) 5:89-98).

SUMMARY OF THE INVENTION

The present disclosure provides a composite hydrogel comprising a blend of an aqueous solution of an anionic polysaccharide or a derivative thereof, in particular hyaluronan or a derivative thereof and methylcellulose or other water soluble cellulose derivative which is inverse thermal gelling and that gels through hydrophobic interactions, together with dispersed hydrophobic polymeric particles selected from microparticles and nanoparticles. In the hydrogel composite, some or all of the dispersed hydrophobic polymer particles may be encapsulated microparticles or nanoparticles that comprise at least one therapeutic agent and each of the at least one therapeutic agents has its own linear sustained release profile. Each therapeutic agent may be released independently, and when the one or more therapeutic agents are encapsulated, a tunable release rate is provided that is a sustained linear release profile from a hydrogel composite with enhanced stability.

In another aspect, the disclosure provides a method for manufacturing a hydrogel composite which comprises the steps of 1) providing an aqueous solution of methylcellulose or other cellulose derivative; 2) mixing an anionic polysaccharide or a derivatives thereof, which may be hyaluronan or a derivative thereof into the aqueous solution; 3) dispersing hydrophobic polymeric particles selected from micro particles and nanoparticles into the aqueous solution to form a stable hydrogel composite that has enhanced stability relative to a hydrogel without the dispersed particles. In another form of this method, the dispersed hydrophobic polymer particles may be encapsulated micro particles or nanoparticles that comprise at least one therapeutic agent and each of the at least one therapeutic agents has its own linear sustained release profile.

In another aspect of the present disclosure, there is provided a method for the treatment of spinal cord injury comprising delivering into the intrathecal space, a composite hydrogel an anionic polysaccharides or a derivatives thereof, such as hyaluronan or a derivative thereof and methylcellulose or other water soluble cellulose derivative, and at least one therapeutic agent selected from FGF2, FGF1, vascular endothelial growth factor (VEGF) and platelet derived growth factor (PDGF) dispersed in the composite hydrogel as microparticles and nanoparticles and/or as encapsulated microparticles and nanoparticles to provide a linear sustained release profile of the at least one therapeutic agent to the injured spinal cord to promote endothelial cell proliferation and blood vessel formation.

Surprisingly, the stability of the hydrogel with the polymeric particles dispersed therein is enhanced relative to the stability of the hydrogel alone. In this form, the hydrogel composite may be used as a bulking agent for reconstructive or cosmetic surgery or as a lubricating agent, or matrix for in situ tissue growth. Because methylcellulose is currently used in food, the hydrogel composite could be used, for example in molecular gastronomy.

The stability of the hydrogel composite is highly advantageous and unexpected as it offers a stable composite without a therapeutic agent or a stable composite for simultaneous delivery of therapeutic agents that has been shown to be stable for periods of up to 50 days.

In the aforementioned pending, parent U.S. patent application Ser. No. 11/410,831, it was thought release would be tuned by altering the properties of the encapsulating polymer. Examples of these properties are: polymer degradation rate, molecular weight; particle porosity, size; and drug load. Drug release from the resulting composite was not expected to differ substantially from drug release from the particles alone. This is because HAMC (the gel) presents a minimal diffusive barrier to drug release. This is also the case with HMW (high molecular weight) HAMC in the present disclosure when a drug is dissolved in the hydrogel: as release is fast and occurs by Fickian diffusion. Unexpectedly, when hydrophobic PLGA particles containing a therapeutic agent were dispersed in HMW HAMC to form composite HMW HAMC it was found that the particles and gel interacted synergistically to alter drug release. As seen in the accompanying drawings, release of particle encapsulated drugs from composite HMW HAMC is significantly slower and more linear than release from the same particles in aqueous suspension. This previously unidentified interaction provides an additional mechanism to alter the release of particle encapsulated drugs that is not dependent on particle or gel formulation. This is advantageous because existing methods in the field to sustain and linearize drug release negatively impact the utility of the drug delivery platform. For example, if drug release is sustained through alteration to the encapsulating polymer, the deliverable drug load is reduced or particle size is increased. This reduces therapeutic efficacy or injectability, respectively. Alternatively, if drug release is slowed by reducing diffusivity through hydrogel, for example by using high concentrations of gel forming polymer, injectability is reduced and gel stiffness may be increased. Increased gel stiffness may be detrimental when the device is brought in contact with soft tissue. Necrosis and scarring of biomaterial contacting tissue has been recorded when the biomaterial is stiffer than the adjacent tissue. Thus, the interaction of HAMC with drug loaded hydrophobic polymer particles maximizes the deliverable drug load and injectability without undue increase to gel stiffness.

DETAILED DESCRIPTION OF THE PREFERRED EMBODIMENTS

The other water soluble cellulose derivatives may be selected from the group comprising hydroxypropyl methylcellulose, ethylcellulose, 3-O-ethylcellulose, hydroxypropyl methylcellulose phthalate, hydrophobically modified hydroxyethyl cellulose selected from ethyl(hydroxyethyl) cellulose, 6-O-alkylated cellulose, cellulose octanoate sulfate, cellulose lauroate sulfate, cellulose stearoate sulfate, and cationic derivatives thereof, 6-O-benzylcellulose, 2,3-di-O-methyl-6-O-benzylcellulose, 2,3-di-O-benzylcellulose, 2,3-di-O-benzyl-6-O-methylcellulose, 2,3,6-tri-O-benzylcellulose, hydroxypropyl methylcellulose acetate succinate, O-2-

[2-(2-methoxyethoxy)ethoxy]acetyl cellulose, when formulated such that the cellulosic solution is inverse thermal gelling.

The anionic polysaccharide or derivative thereof functions to salt out the water soluble cellulose derivative, lowering the temperature of gelation and to increase the viscosity of the composite immediately after injection during the period of gelation. The anionic polysaccharide or derivative thereof may therefore comprise polycarboxylates, a specific example of which is hyaluronan and its derivatives; xanthan gum, dextran sulphate, and other glycosaminoglycans.

Derivatives of hylaruonan include esters of HA, typically formed by treating quaternary ammonium salt of HA with an esterifying agent. Esterification may be carried out using a number of different classes of alcohols such as aliphatic, cycloaliphatic and heterocyclic. Thus, a number of different derivatives can be synthesized and these derivatives have a wide range of physicochemical properties. Examples of HA esters are described by Campoccia D et al. Fidia Advanced Biopolymers, Albano Terme (PD), Italy. *Biomaterials.* 1998 December; 19(23):2101-27.

Glycosaminoglycans are well known, naturally occurring, polysaccharides containing disaccharide repeating units of hexosamine and hexose or hexuronic acid, and may contain sulfate groups. Representative glycosaminoglycans are: heparin; heparan; chondroitin; keratan; dermatan; and sulfates of such materials. Glycosaminoglycans are rendered anionic when the amine group is other than a quaternary form (e.g. all other than $R_3NH^+$) or when the number of deprotonanted sulphate, carbxoylate, or other anionic moieties are greater than the number of protonated amines.

The anionic polysaccharide or derivative thereof and/or methylcellulose or other water soluble hydrophobic cellulose derivatives may additionally be chemically modified using known methods to bear contain increased functionality. Non-limiting examples of functionality include; carboxylic acid, primary amine, aldehyde, hydrazide, maleimide, thiol, furan, alkyne, azide, alkene, urethane, or primary alcohol. These chemical modifications permit subsequent biological utility, for example through covalent linkage of the anionic polysaccharide or derivative thereof and/or methylcellulose or other water soluble hydrophobic cellulose derivatives to a drug molecule or ligand for cellular interaction. For example, the tethering of opiates to HA [Gianolio, D A., et al *"Hyaluronan tethered opioid depots: synthetic strategies and release kinetics in vitro and in vivo.* Bioconjugate Chem. (2008). September; 19(9):1767-74.] and the tethering of cellular adhesion peptides to HA [Cui, F. Z., et al. *"Hyaluronic acid hydrogel immobilized with RGD peptides for brain tissue engineering.* J. Mater. Sci. Mater. Med. (2006). December; 17(12):1393-401.].

The hydrogel composite when formulated for delivery to a body cavity must meet the following criteria: injectable through a fine needle (via injection delivery) which allows for minimally invasive surgery; fast gelling to ensure localized drug delivery at a site of injury; in situ degradable to avoid additional surgeries for device-removal; and scar formation biocompatible to limit foreign-body reaction.

The gelation temperature of thermal gelling materials as well as the kinetics of gelation is concentration dependent. Immediately upon injection of a temperature sensitive polymer into a fluid filled cavity, the polymer disperses prior to gelling. The dispersion causes the gelation rate to decrease. This phenomenon also occurs with chemically cross-linked gels where the kinetics are concentration dependent. To overcome this obstacle, it is necessary to have a highly viscous material so that once injected, will not disperse and thereby suffer from a decreased gelation rate. At the same time, however, the viscous material must still be injectable and this can be achieved with the use of a shear-thinning material. Blending a highly negatively charged anionic polysaccharide or derivative thereof with an inverse thermal gelling polymer like methylcellulose or other cellulose water soluble derivatives at certain molar ratios can achieve this effect.

The anionic polysaccharides or derivatives introduced above may have a molecular weight range of between about 100,000 and about 7,000,000 kg/mol. Hyaluronan and derivatives of hyaluronan may be employed. Exemplified herein is hyaluronic acid (HA). HA is a linear polysaccharide composed of repeating disaccharide units of N-acetyl-glucosamine and D-glucuronic acid. HA forms highly viscoelastic and shear-thinning solutions and has been used for drug delivery, tissue engineering applications as well as for soft tissue augmentation. HA is known to have wound-healing effects such as anti-inflammation, as well as to minimize tissue adhesion and scar formation. It is degraded enzymatically by hyaluronidase, which can be produced by all cells. Its polymeric chains, of lengths 10-15 thousand disaccharides, form random coils with large spheroidal hydrated volumes of up to 400-500 nm in diameter. Because of the high solubility of HA in water, it must be chemically modified or blended with a gelling polymer to form a gel. Chemical modification can occur at the carboxyl group or the hydroxyl group of HA and also at the amino group when the N-acetyl group is removed. Blends of unmodified HA with a gelling polymer are injectable upon an application of force to a syringe because the shear-thinning properties of HA cause the polymer chains to straighten and align themselves permitting flow through the needle. HA then returns to its high viscosity, zero shear structure upon exiting the needle as the polymeric chains once again become entangled amongst themselves.

The methylcellulose or other water soluble cellulose are inverse thermal gelling polymers capable of gelling upon an increase in temperature. The methyl cellulose or other water soluble cellulose may have a molecular weight in the range of between about 2000 and about 1,000,000 g/mol. Exemplary of other suitable polymers include a chitosan and quadrature-glycerophosphate solution, collagen, a tri-block copolymer of poly(ethylene glycol)-poly(lactic-co-glycolic acid)-poly (ethylene glycol), a tri-block copolymer of polypropylene glycol)-poly(ethylene glycol)-poly(propylene glycol), poly (N-isopropyl acrylamide), copolymers of poly-N-isopropylacrylamide, polysaccharides and mixtures thereof.

Exemplified herein is methylcellulose (MC), a carbohydrate and derivative of cellulose. MC is an example of a temperature sensitive gel, or a thermally reversible gel, that gels upon increase in temperature. When the degree of substitution of hydroxyl groups with methyl groups is between 1.4-1.9, methylcellulose has inverse thermal gelling properties whereby it gels upon an increase of temperature. As the temperature increases, hydrogen bonds with the surrounding solvent break and hydrophobic junctions form to produce a gel. Methylcellulose generally forms weak gels at 37° C. when in water, but the gelation temperature can be decreased by an increase in salt concentration. This occurs because the water molecules surround the salts, effectively reducing the number of polymer-solvent interactions. Methylcellulose has previously been considered as a scaffold for experimental traumatic brain injury where in vivo tests in rats indicated biocompatibility over a span of two weeks. MC has also been used as a scaffold in the peripheral nervous system for nerve regeneration with promising results, without any adverse pathological reactions over 8 weeks. Although it is not found to degrade enzymatically, the weak gel structure does dissolve at 37° C. and swells minimally.

Through the manipulation of polymer structure, concentration, and molecular weight, the hydrogel composites may not be in gel form at the time of administration or formation, however, they do form gels with an increase in temperature such as to body temperatures.

To take advantage of the thermal gelling properties of MC and the shear-thinning properties of HA, MC and HA are blended. The combination of an aqueous solution of MC and lyophilized HA results in dispersal of HA within the solution. The resulting hydrogel composite is comprised of dissolved MC and dissolved HA. It is a fast-gelling polymer and is referred to as HAMC. Methods of blending polymer matrices for drug delivery are well known. In general, methods to prepare HAMC involve preparation of a sterile solution of MC in a buffered salt solution, which is cooled to 4° C. prior to the addition of sterile, lyophilized HA which dissolves over time. Because of the high viscosity of this material prior to gelation, HAMC does not flow significantly at room temperature. This allows the polymer blend to maintain some structure as it gels. It is expected that since HA strongly interacts with the solvent, the presence of HA in a MC solution likely dehydrates the MC, similar to the effect of salt on MC gelation, effectively decreasing the gelation temperature. Hence, HA also functions to lower the gelation temperature of MC.

HAMC is unique amongst reversible physical hydrogels in its ability to return to the gel state more rapidly after injection. Typically, physical gelling polymers undergo a phase transition from a solution to a gel after injection whereas HAMC can be formulated such that it is a gel both prior to and following injection. The shear thinning properties of HA enable the HAMC gel to be injectable while the thermal gelling properties of MC return HAMC to a gel following injection. The properties of the gel are highly sensitive to the amount of HA, and altering the concentration of HA would be expected to affect the injectability of the hydrogel composite and the gelation rate. For example, higher molecular weights of HA are likely to have enhanced shear thinning properties. Varying the concentrations of the individual polymers as well as the use of polymers of different molecular weights enhances the properties of the hydrogel composite for injectable delivery.

The hydrogel composite of this invention can be used to target delivery of a pharmaceutical agent, particularly by means of injection. It is well known in the art that pharmaceutical agents can be loaded into polymer matrices with high loading efficiency while retaining the agent's bioactivity. Common methods include imbibing the pharmaceutical agents into pre-formed matrices or incorporating the pharmaceutical agent in the preparation of the polymer matrix itself [Liang et al. Biomacromolecules 5:1917-1925 (2004), Cho et al. Int. J. Pharmaceutics 260:83-91 (2003), Kim et al. J. Controlled Release 80:69-77 (2002)]. For HAMC, both methods will work. Preferably, the therapeutic agent(s), protein(s) or peptide(s) will have some solubility in the MC solution prior to the addition of HA. The solution is maintained overnight to allow the HA to completely dissolve in the solution. The injectable hydrogel composite of this invention provides the following advantages: localized drug release, improved drug distribution, and controlled release rates. Localised drug release at the site of injury enhances therapeutic efficacy, thereby minimizing the risks of systemic toxicity and side effects. Since less drug is lost systemically, localized release also allows for lower doses of drug to be released for therapeutic efficacy. Drug distribution is improved through the localized delivery and by sustained release rates. The advantage offered by the current hydrogel composite is enhanced stability and a release profile that is linear and can be determined based on the particles incorporated therein.

In a specific form of the hydrogel composite, the hyaluronan or a derivative thereof may comprise from about 100 to about 7,000 kg/mol and the methylcellulose or a derivative thereof may comprise from about 1,500 to about 3,000 kg/mol. More particularly the hyaluronan or a derivative thereof may comprise from about 1500 to about 3000 kg/mol and the methylcellulose or a derivative thereof may comprise from about 10 to about 400 kg/mol. When other combinations are used to form the hydrogel composite these amounts can be readily adjusted. This applies to all the ratios, quantities provided hereafter.

In this specific hydrogel composite, the ratio of hyaluronan or a derivative thereof to the methylcellulose or a derivative thereof may comprise from about 1:20 to about 1:1 w/w, more particularly the ratio of hyaluronan or a derivative thereof to the methylcellulose or a derivative thereof may comprise from about 1:5 to about 2:3 w/w.

The ratio of hyaluronan or a derivative thereof in this hydrogel composite may comprise from about 0.5% to about 5.0% by weight and the methylcellulose or a derivative thereof may comprise from about 1.0% to about 10% by weight of the composite. More particularly, the amount of hyaluronan or a derivative thereof may comprise from about 1.0% to about 2.0% by weight and the methylcellulose or a derivative thereof may comprise from about 3.0% to about 7.0% by weight, based on the composite.

The polymeric particles may be hydrophobic polymer particles selected from degradable polymers selected from the group consisting of aliphatic polyesters, aliphatic-aromatic polyesters, aliphatic polyamides, amide ester copolymers, urethane ester copolymers, urethane amide copolymers and urea ester copolymers; and from non-degradable polymers selected from the group consisting of cellulose, starch, polystyrene, polyethylene, polypropylene, and alkylated poly (acrylates). The encapsulated therapeutic agents may be prepared in a known manner in the art. Exemplified here are therapeutics that have been encapsulated in poly(lactic-co-glycolic acid) (PLGA) microparticles and nanoparticles. Hydrogels containing polymer particles are denoted composite hydrogels.

As used herein, "microparticles" refers to particles having a diameter of less than 1.0 mm, and more specifically between 1.0 and 100.0 microns. Microparticles include microspheres, which are typically solid spherical microparticles. Microparticles also include microcapsules, which are spherical microparticles typically having a core of a different polymer, drug, or composition.

As used herein, "nanoparticles" refers to particles or structures in the nanometer range, typically from about 1 nm to about 1000 nm in diameter, which are encapsulated within the polymer.

Lipid/polymer liposomes and polymeric microspheres are known in the art. A method of producing such lipid/polymer liposomes is described, for example, in U.S. Pat. No. 6,277,413.

Suitable biodegradable polymers for producing the microparticles are polyesters such as polylactide, polyglycolide, copolymers of lactide and glycolide, polyhydroxybutyrate, polycaprolactone, copolymers of lactic acid and lactone, copolymers of lactic acid and PEG, copolymers of α-hydroxy acids and α-amino acids (polydepsipeptides), polyanhydrides, polyorthoesters, polyphosphazenes, copolymers of hydroxybutyrate and hydroxyvalerate, poly ethylene carbonate), copoly(ethylene carbonate), polyethyleneterephthalate or mixtures of these polymers. Examples of resorbable/biodegradable polymers are lactide homopolymers poly(L-lactide), poly(D,L-lactide), and copolymers of lactide and glycolide such as 50:50 poly(DL lactide co-glycolide)(PLG). While polyethylene glycol (PEG) is the preferred water soluble polymer for mixing with the biodegradable polymer, other suitable water soluble polymers include poly(oxyethylene oxide)(PEO), poly(oxyethylene)-poly(oxypropylene) [PEO-PPO] block copolymers such as tri-block PEO-PPO-PEO copolymers (Poloxamers, Pluronics) and tetra-functional block copolymers derived from the sequential addition of propylene oxide and ethylene oxide to ethylene diamine (Poloxamines, Tetronics), copolymers of PEG with poly(lactic acid), oligomers of poly(lactic acid), lactides, copolymers of PEG and amino acids, conjugates of PEG with polysaccharides for example a conjugate produced from 40000 MW dextran and polyoxyethylene-glycol monomethyl ether and others as described by Duval et al. in Carbohydrate Polymers, 15, (1991), 233-242, conjugates of PEG with proteins such as those described by Nucci et al., in Advances in Drug Delivery Review, 6, (1981), 113-151, or with collagen as described by Rhee et al in Poly(ethylene glycol) chemistry. Biotechnical and Biomedical Applications. Ed. J. Milton Harris, Plenum Press (1992), or conjugates of PEG with colony Stimulating Factor (CSF-1) as described by Katre N. V. in The conjugation of proteins with polyethylene glycol and other polymers. Adv. Drug Delivery Reviews, 10, 91-114 (1993).

Suitable biocompatible, non-biodegradable polymers include, but are not limited to, polyacrylates; ethylene-vinyl acetates; acyl substituted cellulose acetates; non-degradable polyurethanes; polystyrenes; polyvinyl chlorides; polyvinyl fluorides; poly(vinyl imidazoles); chlorosulphonate polyolefins; polyethylene oxides; or blends or copolymers thereof.

To form microspheres, in particular, a variety of techniques known in the art can be used. Methods of producing microspheres are described, for example, in U.S. Pat. Nos. 5,552,133; 5,310,540; 4,718,433; and 4,572,203; European Patent Publication No. EP 458,745; and PCT Publication No. WO 92/05806. Methods include, for example, single or double emulsion steps followed by solvent removal. Solvent removal may be accomplished by extraction, evaporation or spray drying among other methods.

In the solvent extraction method, the polymer is dissolved in an organic solvent that is at least partially soluble in the extraction solvent such as water. The bioactive molecule, either in soluble form or dispersed as fine particles, is then added to the polymer solution, and the mixture is dispersed into an aqueous phase that contains a surface-active agent such as poly (vinyl alcohol). The resulting emulsion is added to a larger volume of water where the organic solvent is removed from the polymer/bioactive agent to form hardened microparticles.

In the solvent evaporation method, the polymer is dissolved in a volatile organic solvent. The bioactive molecule, either in soluble form or dispersed as fine particles, is then added to the polymer solution, and the mixture is suspended in an aqueous phase that contains a surface-active agent such as poly (vinyl alcohol). The resulting emulsion is stirred until most of the organic solvent evaporates, leaving solid microspheres.

In the spray drying method, the polymer is dissolved in a suitable solvent, such as methylene chloride (e. g., 0.04 g/ml). A known amount of bioactive molecule (drug) is then suspended (if insoluble) or co-dissolved (if soluble) in the polymer solution. The solution or the dispersion is then spray-dried. Microspheres ranging in diameter between one and ten microns can be obtained with a morphology, which depends on the selection of polymer.

Other known methods, such as phase separation and coacervation, and variations of the above, are known in the art and also may be employed in the present invention.

Formulation of nanoparticles can be achieved essentially as described above for microparticles except that high speed mixing or homogenization is used to reduce the size of the polymer/bioactive agent emulsions to below about 2.0 microns, preferably below about 1.0 micron. For example, suitable techniques for making nanoparticles are described in PCT Publication. No. WO 97/04747.

In the examples presented herein, in the case of the dispersed hydrophobic polymeric particles, the particle load may comprise from about 1 to about 20 wt %, more particularly from about 2.5 to about 10 wt %, based on the composite. In the case where some or all of the dispersed hydrophobic polymer particles are encapsulated micro particles or nanoparticles that comprise at least one therapeutic agent, the dispersed particle load may comprise from about 1 to about 20 wt %, more particularly from about 10 to about 20 wt %, based on the composite.

In the examples presented herein the hydrophobic polymeric particles may have particle sizes selected from particle sizes of about 150 nm to about 40 μm, and more particularly, from about 220 nm to about 830 nm. When the particles include the at least one therapeutic agent, the particle sizes are selected to provide the desired release profile. A suitable sustained release profile has been found to be provided by dispersing polymeric particles selected from particle sizes of from about 220 nm to about 37 μm.

The delivered therapeutic agent load from the encapsulated particles is generally in the range of about 0.1 to about 30 wt % (drug mass as a percentage of the drug loaded particle mass), and more particularly in the range of from about 1.0 to about 10 wt % (drug mass as a percentage of the drug loaded particle mass).

The aqueous solution of hyaluronan or a derivative thereof and methylcellulose or other cellulose derivative may be selected from the group comprising water, saline, artificial cerebrospinal fluid, and buffered solutions.

The drug delivery hydrogel composite of this invention has multiple applications and may be delivered via injection, transdermal, oral, sub-cutaneous, intranasal, vaginal, buccal, intrathecal, subdural, epidural, ocular space, dental, intratumoral, intramuscular, intraarticular, and intraveneously. The drug delivery synergistic hydrogel composite is designed for delivery into a fluid-filled (or partially-filled) cavity. These include all cavities throughout the body, including but not limited to the intrathecal space, the intra-articular cavity, among others.

The hydrogel composite components can be modified to alter the degradation rate of the hydrogel composite and, hence, affect the rate of release of the pharmaceutical agent from the hydrogel composite. One such modification involves addition of salts to alter the pH. Since the charge of the anionic gelling polymer causes its viscosity to be pH sensitive, it is possible that the hydrogel composite blend is also pH sensitive. The pH can be varied to control properties such as formulation for delivery or processing. A pH-sensitive hydrogel composed of methylcellulose and alginate was previously demonstrated by Liang et al. (Biomacromolecules 5:1917-1925, 2004) to be capable of increased load release at a higher pH (pH 7.4) compared to a lower pH (pH 1.2). Blending of the hydrogel composite with a salt could be performed to achieve a pH-dependent delivery vehicle.

Another alternative to creating a more stable gel for slower degradation is to functionalize the polymers with thiol groups and acrylate groups. The hydrogel composite is injected and gels quickly at the site of injection because, at physiological conditions, a Michael-type addition reaction occurs between the polymer end terminated with thiol and the polymer terminated with acrylate chains. This technique results in a product that is fast gelling with a high degree of gel strength, achieved as a result of linking multiple crosslinked polymers. For example, using a methacrylated polymer, such as methacrylated dextran, and a thiol conjugated polymer, such as PEG-dithiol or a peptide-dithiol, a crosslinked dextran gel can be achieved. Using a specific amino acid sequence that is enzymatically cleaved, a degradable, injectable crosslinked polysaccharide gel can be synthesized.

Another method of controlling degradation rates is to increase the hydrophobicity of HA, which helps to maintain the integrity of gel through the formation of more hydrophobic junctions resulting in less water penetration. To render HA more hydrophobic, the reactive functional groups, hydroxyl or carboxyl, can be modified with hydrophobic molecules. For example, it is possible to modify the carboxyl group of HA with acetic hydrazide using standard coupling agents, such as carbodiimides like EDC. It should be noted that the carboxyl group is important for the highly viscous nature of the hydrogel composite.

Another means to enhance sustained release of the pharmaceutical agent is to take advantage of ionic interactions between the agent and the polymer. The highly negatively charged anionic gelling polymer engages in ionic interactions with positively charged molecules. In cases where there is no significant drug-polymer interaction or the charges are the same such that there are no attractive forces, the charge can be modified with the use of charged stabilizers. Cationic particles or a mixture of cationic and anionic particles are used within the anionic gelling polymer to prevent the particles from dispersing away from the gel, as well as to promote increased gel strength through ionic crosslinks. Methods for incorporating cationic or cationic/anionic charge stabilizers into pharmaceutical compositions may be employed and are known to those of skill in the art. Examples are known in the art [Schexnailder, P. and G. Schmidt, *Nanocomposite polymer hydrogels*. Colloid And Polymer Science, 2009. 287(1): p. 1-11. Hooper, J. B. and K. S. Schweizer, *Theory of phase separation in polymer nanocomposites*. Macromolecules, 2006. 39(15): p. 5133-5142. Hooper, J. B. and K. S. Schweizer, *Contact Aggregation, Bridging, and Steric Stabilization in Dense Polymer-Particle Mixtures*. Macromolecules, 2005. 38: p. 8858-8869.]

Another alternative to further controlling drug release is by tethering or covalently bonding the pharmaceutical agent to the polymer. The agent releases from the hydrogel composite upon breakage of the covalent bond or upon dissolution of the chain from the hydrogel composite network. Methods of covalently bonding pharmaceutical agents to polymers may be employed and are known to those of skill in the art. Examples are described in Hoffman et al. (Clinical Chemistry 46(9):1478-1486).

Chitosan, an amino-polysaccharide, is another example of an inverse thermal gelling polymer that can be used in the hydrogel composite. It is obtained by the alkaline deacetylation of chitin. Chitosan is both biocompatible and biodegradable and has inherent wound healing properties, in addition to a wide range of applications in drug delivery and tissue engineering. Chitin and chitosan are generally found as copolymers, and it is the chitin segments that are enzymatically degradable by lysozyme. It is a cationic polymer which is soluble in acidic conditions. Recently, Chenite et al. (Biomaterials 21:2155-2161, 2000) developed a thermogelling polymer by mixing beta-glycerophosphate (quadrature-GP) into a chitosan solution. Chitosan/beta-GP gels upon an increase in temperature where the gelation temperature is affected by both pH and beta-GP concentration. The negatively charged beta-GP molecules are attracted to the positively charged amine groups of chitosan, preventing chitosan from aggregating and precipitating at physiological pH. Upon an increase in temperature, a gel is formed because of the formation of physical junction zones which occur when hydrophobic and hydrogen bonding forces outweigh the interchain electrostatic repulsion forces.

It is possible to alter the rate of degradation of the composite by increasing the hydrophobicity of hyaluronan or the derivative thereof. More specifically, an altered rate of degradation rate may be provided by the addition of at least one functional group to the hyaluronan or the derivative thereof or the methylcellulose or other cellulose derivative selected from the group consisting of carboxylic acid, primary amine, aldehyde, hydrazide, maleimide, thiol, furan, alkyne, azide, alkene, urethane, and primary alcohol.

The therapeutic agent may be encapsulated in a microsphere, nanoparticle or liposome. A charge stabilizer may be added to promote an interaction between the blend and the therapeutic agent. The therapeutic agent may be covalently bonded to the hyaluronan or the derivative thereof.

Non-limiting examples of the therapeutic agent include, but are not limited to the group of therapeutic agents comprising anaesthetics for use in caudal, epidural, inhalation, injectable, retrobulbar, and spinal applications; analgesics, selected from the group comprising acetaminophen, baclofen, ibuprofen, fluriprofen, ketoprofen, voltaren, phenacetin and salicylamide; anti-inflammatories selected from the group comprising naproxen and indomethacin; antihistamines, selected from the group comprising chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group comprising dextromethorphan hydrobromide and guaifenesin; expectorants; decongestants, selected from the group comprising phenylephrine hydrochloride, phenylpropanolamine hydrochloride, pseudoephedrine hydrochloride, and ephedrine; antibiotics selected from the group comprising amebicides, broad and medium spectrum, fungal medications, monobactams and viral agents; bronchodilators selected from the group comprising theophylline, albuterol and terbutaline; cardiovascular preparations selected from the group comprising diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides; central nervous system drugs selected from the group comprising thioridazine, diazepam, meclizine, ergoloid mesylates, chlorpromazine, carbidopa and levodopa; metal salts selected from the group comprising potassium chloride and lithium carbonate; minerals selected from the group consisting of iron, chromium, molybdenum and potassium; immunomodulators; immunosuppresives selected from the group comprising minocycline, cyclosporine A; thyroid preparations selected from the group comprising synthetic thyroid hormone, and thyroxine sodium; peptide and glycoprotein hormones and analogues selected from the group comprising human chorionic gonadotrophin (HCG), corticotrophin, human growth hormone (HGH-Somatotrophin) and erythropoietin (EPO); steroids and hormones selected from the group comprising ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP, and others; vitamins selected from the group comprising water-soluble vitamins and veterinary formulations; growth factors selected from the group comprising EGF, FGF2 and neurotrophin; peptides, peptide mimetics and other protein preparations; DNA; and, small interfering RNAs; with or without a pharmaceutically acceptable carrier or preservative.

DETAILED EMBODIMENTS

The present disclosure may be understood more readily by reference to the following detailed description taken in connection with the accompanying figures and examples, which form a part of this disclosure. It is to be understood that this disclosure is not limited to the specific compositions, methods, conditions or parameters described and/or shown herein, and that the terminology used herein is for the purpose of describing particular embodiments by way of example only and is not intended to be limiting of the claims.

Exemplified herein are biocompatible and biodegradable blends of 2 wt % hyaluronan and 7 wt % methylcellulose (2:7 HAMC) using specific molecular weights of HA and MC, and biocompatible and biodegradable blends of between 1-3 wt % HA with 3% MC using a second pair of polymer molecular weights. The later pair of molecular weights are denoted "high molecular weight (HMW)" relative to the former. The role of MC is to form a physical hydrogel through hydrophobic junctions and HA to increase solution viscosity and to enhance MC gel strength at lower temperatures through the salting out effect. Additionally, based on the anti-inflammatory action of HA, this component is likely responsible for the beneficial, anti-inflammatory effect of 2:7 HAMC in a compression model of SCI. 2:7 HAMC was found to degrade within 4-7 days in vivo, making it well suited for neuroprotective delivery strategies but unsuitable for drug delivery over longer time periods (ie. 1-4 weeks) weeks necessary for regenerative strategies. Accordingly, these injectable hydrogels were used to deliver erythropoietin, as well as EGF and FGF-2 via simple diffusion. For soluble molecules, the release profile is determined principally by diffusivity and occurs within 24 hours due to the short diffusive path length in vivo.

EXAMPLES

Figure 1:
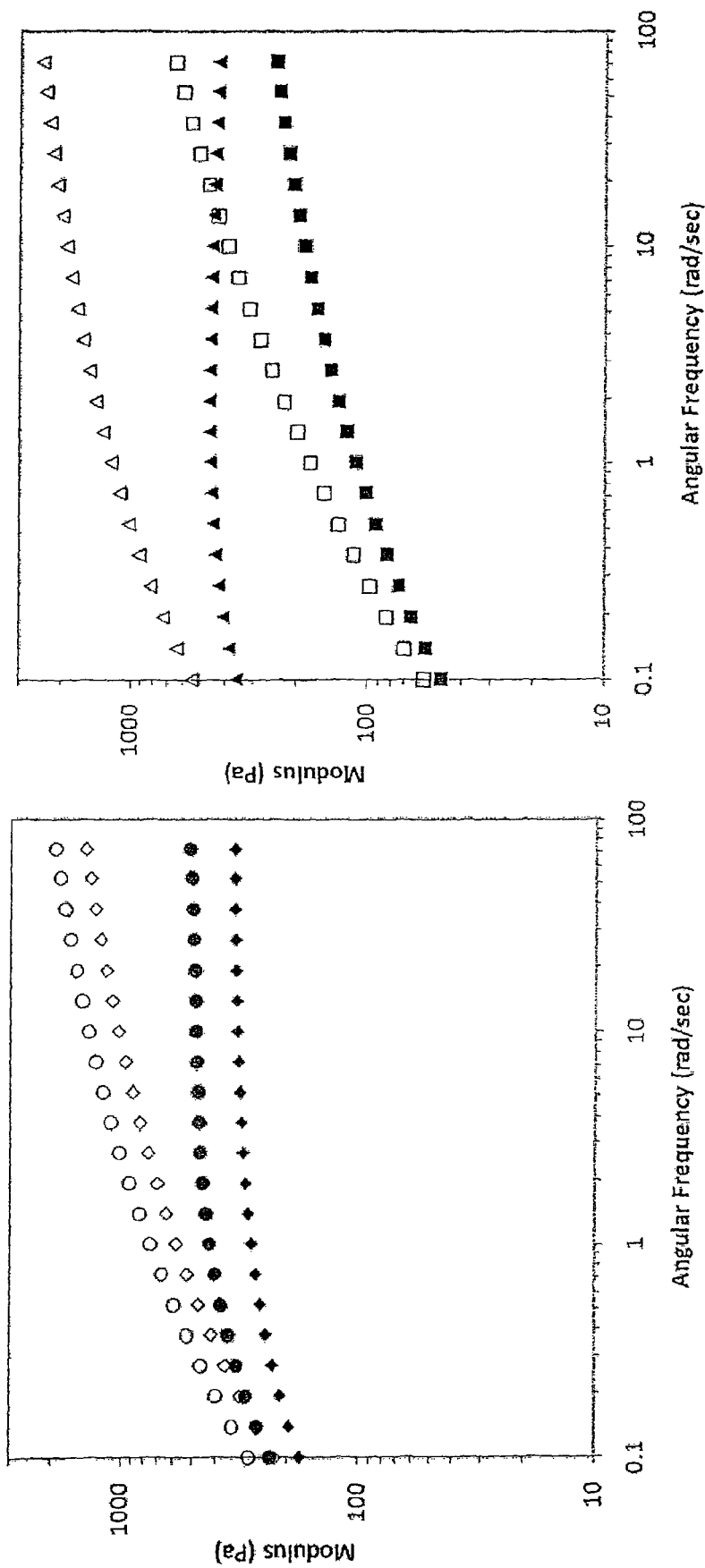
FIG. 1 illustrates that the rheological behaviour of certain HMW HAMC formulations are similar to that of 2:7 HAMC. Similar G' and G" values indicate comparable injectability. The frequency sweeps were conducted at 37° C. Storage (G', open symbols) and loss modulus (G", filled symbols) of injectable gels are represented. 2:3 HMW HAMC (◇) and 2:7 HAMC (○) are gels are shown in the left graph. 1:3 HMW HAMC (□) and 3:3 HMW HAMC (Δ) are shown in the right graph.

The present release formulation provides longer term release suitable for combination neuroregenerative and neuroprotective strategies. High molecular weight blends of hyaluronic acid (HA) or a derivative thereof and methylcellulose (MC) (HMW HAMC) which remain injectable and are stable for more than 28 days in vitro are described. To achieve longer-term release profiles, formulations of drug loaded poly (lactic-co-glycolic acid) (PLGA) nano- and micro particles were dispersed in the HMW HAMC gel. Use of the drug delivery platform was demonstrated using six therapeutic molecules or models thereof, shown in Table 1, for periods of between 1 and 28 days. This contribution demonstrates the composite HMW HAMC hydrogel is a flexible, localized drug delivery platform for the evaluation of therapies targeting protection and repair of the injured spinal cord.

TABLE 1

Molecules released from HMW HAMC

| Molecule (model) | Molecular Weight (kg/mol) | Neuro-protective | Neuro-regenerative | Desired Treatment Term |
|---|---|---|---|---|
| NBQX | 0.336 | * | | days |
| dbcAMP | 0.469 | | * | weeks |
| EGF | 6.2 | | * | weeks |
| FGF-2 | 17 | * | * | days |
| Neurotrophin-3 (α-Chymotrypsin) | 29 (25) | | * | weeks |
| Anti-NogoA (IgG) | 150 (150) | | * | weeks |

Recombinant human basic fibroblast growth factor (FGF-2, >95% wt) was purchased from Biovision (Santa Clara, USA). 2,3-Dioxo-6-nitro-1,2,3,4-tetrahydrobenzo[f]quinoxaline-7-sulfonamide disodium salt (sodium NBQX, >98% wt) was purchased from A.G. Scientific (San Diego, USA). α-Chymotrypsin (type II from bovine pancreas), human IgG, and $N^6,2'$-O-dibutyryladenosine 3′,5′-cyclic monophosphate sodium salt (dbcAMP) were purchased from Sigma-Aldrich (Oakville, Calif.). Recombinant human epidermal growth factor (EGF) was purchased from Peprotech™ (Rocky Hill, USA).

Sodium hyaluronate of 1700 kg/mol was purchased from FMC Biopolymer (Sandvika, Norway) and of 2600 kg/mol from Lifecore (Chaska, USA). Methylcellulose of 300 kg/mol was purchased from Shin-Etsu (Tokyo, Japan). Poly (DL-lactic-co-glycolic acid) 50:50 of inherent viscosity 0.15-0.25 dL/g and methylcellulose (13 kg/mol) were purchased from Sigma-Aldrich. Poly(DL-lactic-co-glycolic acid) 50:50 of inherent viscosity 0.20 dL/g and 0.37 dL/g were purchased from Durect (Cupertino, USA). Poly(vinyl alcohol), 6 kg/mol and 80% mol hydrolyzed, was purchased from Polysciences Inc. (Warrington, USA). Polystyrene (220 nm, 510 nm, 830 nm, 3.09 µm, 15.5 µm) and poly(acrylic acid) (60 nm) particles were received as suspensions in water from Bangs Laboratories (Fishers, USA), scrubbed of surfactant by exposure to cation exchange resin (Amberlyst-15, Sigma-Aldrich), neutralized with 1M NaOH and lyophilized (Labconco, Kansas City, USA) prior to use.

HPLC grade dichloromethane (DCM) and dimethyl sulfoxide (DMSO) were supplied by Caledon Labs (Georgetown, Calif.). All buffers were made with distilled and deionized water prepared using a Millipore Milli-RO 10 Plus and Milli-Q UF Plus at 18 MΩ resistance (Millipore, Bedford, USA). Phosphate buffered saline powder was purchased from MP Biomedicals (pH 7.4, 9.55 g/L, Solon, USA). Artificial cerebrospinal fluid (aCSF) at a pH of 7.4 was prepared as previously described [Gupta, D., C. H. Tator, and M. S. Shoichet, *Fast-gelling injectable blend of hyaluronan and methylcellulose for intrathecal, localized delivery to the injured spinal cord*. Biomaterials, 2006. 27(11): p. 2370-9]. All other solvents and reagents were supplied by Sigma-Aldrich and used as received.

Preparation of HAMC Hydrogels and Composite Hydrogels

Physical hydrogel blends of hyaluronan (HA) and methylcellulose (MC) were prepared in the following compositions in aCSF; 2 wt % 1700 kg/mol HA, 7 wt % 13 kg/mol MC (2:7 HAMC); 1 wt % 2600 kg/mol HA, 3 wt % 300 kg/mol MC (1:3 HMW HAMC); 2% 2600 kg/mol HA, 3 wt % 300 kg/mol MC (2:3 HMW HAMC); and 3 wt % 2600 kg/mol HA, 3 wt % 300 kg/mol MC (3:3 HMW HAMC). In each case MC was mechanically dispersed using a planetary mixer (Flacktek Inc., Landrum, USA) and left to dissolve overnight at 4° C. HA was then added to the MC solution, dispersed, and dissolved in the same way. Cold solutions were centrifuged to remove entrained bubbles, resulting in transparent hydrogels.

Drug loaded hydrogels were prepared by dispersing dry drug formulations or concentrated, buffered solutions in HAMC using a planetary mixer and left to dissolve overnight at 4° C. before use. Drug loaded PLGA particles and model polystyrene particles were dispersed in HAMC immediately prior to use.

Rheological Characterization of HAMC Hydrogels

The storage and loss moduli of 2:7 HAMC and the HMW HAMC hydrogels were determined as a function of oscillation frequency on an AR-1000 rheometer fitted with a 40 mm, 2° cone and plate geometry (TA Instruments, New Castle, USA). An amplitude sweep was performed to confirm that the frequency and strain were within the linear viscoelastic region. Temperature was controlled at 37° C. using the integrated Peltier plate and sample evaporation was minimized using a solvent trap. After 5 min equilibration the frequency sweep was conducted from 0.1-100 rad/s at 12% strain for all materials.

In vitro Stability and Swelling of Composite HAMC Hydrogels

Approximately 150 mg of HMW HAMC loaded with 0, 25, or 75 mg/mL of 220 nm or 830 nm polystyrene nanoparticles was deposited into pre-weighed polypropylene sample tubes, weighed, warmed to 37° C., and combined with 800 µL of warm aCSF. Samples were incubated at 37° C. on a rotary shaker at 2 Hz throughout the experiment and the aCSF buffer sampled with total replacement after: 1 hour, 6 hours, and 1, 3, 7, 14, 21, and 28 days. Recovered buffer was sonicated to disrupt residual hydrogel (Sonics, Newtown, USA) and create a uniform nanoparticle suspension. The concentration of 220 nm particles was determined by a turbidity assay at 500 nm on an Agilent 8453™ spectrophotometer (Agilent Technologies, Santa Clara, USA).

The swelling ratio, Q, of HAMC and composites was determined by accurately weighing each gel sample in the stability study after the aCSF had been removed, correcting for residual buffer, and dividing by the original hydrated sample mass. To compare the degradation of composites with different swelling characteristics, normalized Q was defined as:

$$\frac{Q(t)}{Q_{max}} \qquad (1)$$

where $Q_{max}$ is the maximum recorded swelling ratio of the sample.

Determination of Drug Diffusivity in HMW HAMC

The diffusivity of a given drug in HMW HAMC, D, was normalized to its diffusivity in water, $D_o$, to determine the impact of HMW HAMC on molecular diffusion [N. A. Peppas, C. T. Reinhart, *Solute diffusion in swollen membranes. 1. A new theory*. J. Membr. Sci. 15 (3) (1983) 275-287. Approximations of D for NBQX, α-chymotrypsin, and IgG in HMW HAMC were estimated according to the one dimensional, unidirectional, thin film approximation for non-swelling samples at short times [J. Crank, *The Mathematics of Diffusion*, Clarendon Press, Oxford, 1956.]. Normalized diffusion coefficients were then determined with respect to previously reported values of $D_o$ according to:

$$\frac{D}{D_o} = \frac{\pi \left(\frac{M_t}{M_\infty} \frac{l}{2}\right)^2}{D_o t} \qquad (2)$$

Where $M_t/M_\infty$ is the cumulative mass of drug detected at time, t, divided by the total mass released and l is the sample thickness.

Approximately 100 mg of HAMC with a drug loading of 100-1000 μg/mL was deposited into a cylindrical sample tube to yield a gel with thickness of 0.3 cm and one exposed surface. Samples were warmed to 37° C. and combined with 900 μL of warm aCSF. The buffer was sampled with total replacement at 0.5, 1, 2, and 5 hours and analyzed and described below.

Drug Release from HAMC Hydrogels

Release profiles of each particle encapsulated drug were obtained by depositing approximately 150 mg of drug loaded 2:3 HMW HAMC into polypropylene sample tubes, warming to 37° C., and adding 600 μL warm aCSF. Samples were incubated at 37° C. on a rotary shaker at 2 Hz throughout the study and the aCSF buffer sampled with total replacement after 0.5, 1, 3, 7, 14, 21, and 28 days. Particle loads were typically 30-40 mg PLGA per gram of composite. Release profiles of dissolved drugs were obtained in the same manner with more frequent sampling, typically at 0.5, 1, 3, 6, 24, and 72 hours. All sample aliquots were immediately frozen and stored at −20° C. until analysis. IgG, α-chymotrypsin, and EGF concentrations were determined by the bicinchoninic acid assay (BCA) (Thermo Fisher Scientific, Rockford, USA); NBQX and dbcAMP by UV absorbance at 425 and 273 nm, respectively; and FGF-2 by ELISA (R&D Systems, Minneapolis, USA). Each sample was thawed immediately prior to assay and clear supernatant analyzed for dissolved drug.

Preparation and Characterization of Drug Loaded PLGA Particles

PLGA microparticle synthesis was optimized for each factor encapsulated and thus synthesis varied slightly for each factor, described below for EGF, dbcAMP, IgG and α-chymotrypsin. Microparticle size was determined by laser diffraction (Mastersizer 2000™, Malvern Instruments, Malvern, UK): nanoparticle size was determined by dynamic light scattering (Zetasizer Nano ZS™, Malvern Instruments). Encapsulation efficiency was defined as the fraction of drug detected per unit mass of particle compared to the theoretical maximum. Particle yield is the mass of recovered particulate PLGA adjusted for drug content, divided by the initial PLGA mass. Drug loading is the mass fraction of drug in the particles expressed as microgram of drug per milligram of particles.

Preparation of EGF Loaded PLGA Microparticles

EGF loaded microparticles were prepared by a water-oil-water double emulsion (w/o/w) method with an inner aqueous phase of 100 μL, 20 mg/mL EGF in PBS, an organic phase of 1.5 mL, 100 mg/mL PLGA (0.15-0.25 dL/g) in DCM and an outer aqueous phase of 50 mL, 10 mg/mL PVA and 100 mg/mL NaCl. The primary emulsion was created by 10 s of vortexing (Scientific Industries, Bohemia, USA) followed by 15 s of sonication. The secondary emulsion was formed by addition of the outer aqueous phase and homogenization by a Kinematica PT3000™ (Brinkmann, Mississauga, Calif.). The double emulsion was then added to 150 mL of a 100 mg/mL NaCl and 1 mg/mL PVA solution and stirred for 4 h at room temperature. EGF loaded PLGA microparticles were isolated and washed 4 times by centrifugation, lyophilized, irradiated with 2.5 kGy gamma rays, and stored at −20° C.

EGF content was determined by degrading the PLGA in 1 M NaOH for 24 h at 37° C., centrifuging the resulting suspension and assaying the supernatant for total protein using the BCA assay.

Preparation of dbcAMP Loaded PLGA Microparticles dbcAMP loaded microparticles were prepared from a w/o/w double emulsion, with an inner aqueous phase of 75 μL, 267 mg/mL dbcAMP in ddH$_2$O, an organic phase of 600 μL, 217 mg/mL PLGA (0.20 dL/g) in a 75:25 v/v solution of DCM and acetone, and an outer aqueous phase of 25 mL, 25 mg/mL PVA and 100 mg/mL NaCl. The primary and secondary emulsions were created by 45 s of sonication and homogenization, respectively. The double emulsion was then added to 200 mL of a 100 mg/mL NaCl and 2.5 mg/mL PVA solution and stirred for 3 h at room temperature. dbcAMP loaded PLGA microparticles were isolated and washed with ddH$_2$O over a 200 nm nylon filter, lyophilized, irradiated with 2.5 kGy gamma rays, and stored at −20° C.

dbcAMP content was determined by DCM/water solvent extraction. PLGA was dissolved in DCM and extracted 3×. Aqueous dbcAMP concentration was determined by UV absorbance at 273 nm on a Nanodrop ND-1000™ (Thermo Fisher Scientific).

Preparation of IgG and α-Chymotrypsin Loaded PLGA Nanoparticles

IgG loaded nanoparticles were prepared from a w/o/w double emulsion, with an inner aqueous phase of 100 μL, 10 mg/mL IgG in aCSF, an organic phase of 0.9 mL, 50 mg/mL PLGA (0.15-0.25 dL/g) and 0.5 mg/mL Pluronic F-127™ in DCM, and an outer aqueous phase of 3 mL, 25 mg/mL PVA. The primary emulsion was created by 10 min of sonication over ice. The secondary emulsion was formed by addition of the outer aqueous phase and sonication for a further 10 min over ice. The double emulsion was then added to 40 mL of a 25 mg/mL PVA solution and stirred for 20 h at room temperature. α-Chymotrypsin loaded nanoparticles were produced in an identical manner with the addition of 1 mg/mL of DCM to the final aqueous volume prior to combination with the double emulsion. Protein loaded PLGA nanoparticles were isolated and washed 4 times by ultracentrifugation, lyophilized, and stored at −20° C.

Protein content was determined based on a method by Wong [Wong, H. M., Wang, J. J., and Wang, C, *In Vitro Sustained Release of Human Immunoglobulin G from Biodegradable Microspheres*. Ind. Eng. Chem. Res., 2001. 40: p. 933-948]. Briefly, nanoparticles were dissolved in DMSO at 37° C. and then diluted with 50 mM NaOH. The resulting suspension was allowed to settle and the supernatant assayed for total protein using the BCA assay.

Statistical Analysis

Data are expressed as means±standard deviation unless otherwise noted. Comparisons of groups of means were determined by ANOVA and pairs of mean by Student's t-test where appropriate. Significance was assigned at $p<0.05$.

Rheology of Hyaluronan and Methylcellulose Hydrogels

While previous 2:7 HAMC formulations degraded in vivo within 4-7 days [Kang, C. E., et al., *A New Paradigm for Local and Sustained Release of Therapeutic Molecules to the Injured Spinal Cord for Neuroprotection and Tissue Repair*. Tissue Eng Part A, 2008], the goal here was to develop a more stable HAMC for longer term delivery while maintaining the properties of injectability and fast gelation. Higher molecular weight HA and MC provided enhanced stability. Blends of 1-3% HA (2600 kg/mol) and 3% MC (300 kg/mol) met the qualitative criteria of fast gelation and injectability through a 30 G/200 μm inner diameter needle and were compared to 2:7 HAMC by rheology. The frequency sweeps shown in FIG. 1 were conducted at 37° C. and revealed the new compositions were of a similar stiffness to 2:7 HAMC and that 2:3 HMW HAMC was most like the original hydrogel. This observation was of practical importance because the stiffness of 2:7 HAMC approached the upper limit of what can be injected in the intrathecal space using the method described by Jimenez-Hamann, et at [Jimenez Hamann, M. C., et al., *Novel intrathecal delivery system for treatment of spinal cord injury*. Exp Neurol, 2003. 182(2): p. 300-9]. Referring to FIG. 1, it should be noted that Storage (G', open symbols) and loss modulus (G", filled symbols) of injectable gels. 2:3 HMW HAMC (◇) and 2:7 HAMC (○) are gels and behave similarly at low frequencies shown in the left graph. 1:3 HMW HAMC (□) and 3:3 HMW HAMC (Δ) are shown in the right graph.

Hydrogel Swelling & Degradation

As a cross-linked hydrogel containing the polyelectrolyte HA, HAMC swells when placed in a reservoir of aCSF in vitro or CSF in vivo. It was thought possible that an intrathecally injected hydrogel, resting between the pia and arachnoid mater, may put pressure on the spinal cord as the material swells in CSF. The swelling ratio, Q, at early times and maximal swelling ratio, $Q_{max}$, were both of interest because the spinal cord can tolerate larger gel volumes if the swelling force is progressively applied over longer periods [Uchida, K., et al., *Progressive changes in neurofilament proteins and growth-associated protein-43 immunoreactivities at the site of cervical spinal cord compression in spinal hyperostotic mice*. Spine, 2002. 27(5): p. 480-6]. It has previously been demonstrated that injections of 20 µL, of collagen gel or 10 µL, of 2:7 HAMC were safe in a rat model of SCI [Gupta, D., C. H. Tator, and M. S. Shoichet, *Fast-gelling injectable blend of hyaluronan and methylcellulose for intrathecal, localized delivery to the injured spinal cord*. Biomaterials, 2006. 27(11): p. 2370-9, Kang, C. E., et al., *A New Paradigm for Local and Sustained Release of Therapeutic Molecules to the Injured Spinal Cord for Neuroprotection and Tissue Repair*. Tissue Eng Part A, 2008]. Although the maximum safe gel volume in vivo has not been well characterized, the 2:7 HAMC formulation reached a maximum swelling ratio, $Q_{max}$, of 2.2 at 3 days in vitro and was shown to be safe in vivo, suggesting that this value was acceptable. By comparison, at three days the $Q_{max}$ for 1:3 HMW HAMC was 1.4 and 2:3 HMW HAMC was 1.8 whereas 3:3 HMW HAMC was 2.4, nominally higher than 2:7 HAMC. The increase in $Q_{max}$ as a function of HA concentration reflects an increase in osmotic pressure common to polyelectrolytes [Gerdin, B. and R. Hallgren, *Dynamic role of hyaluronan (HYA) in connective tissue activation and inflammation*. Journal of Internal Medicine, 1997. 242(1): p. 49-55]. Swelling at early times, shown at 6 hours in FIG. 3, was similarly comparable between 2:7 HAMC and the HMW HAMC blends. The three HMW HAMC formulations met the swelling criteria, permitting an in vivo injection volume of ~10 µL, and maximum gel volume similar to 2:7 HAMC over time.

Figure 2:
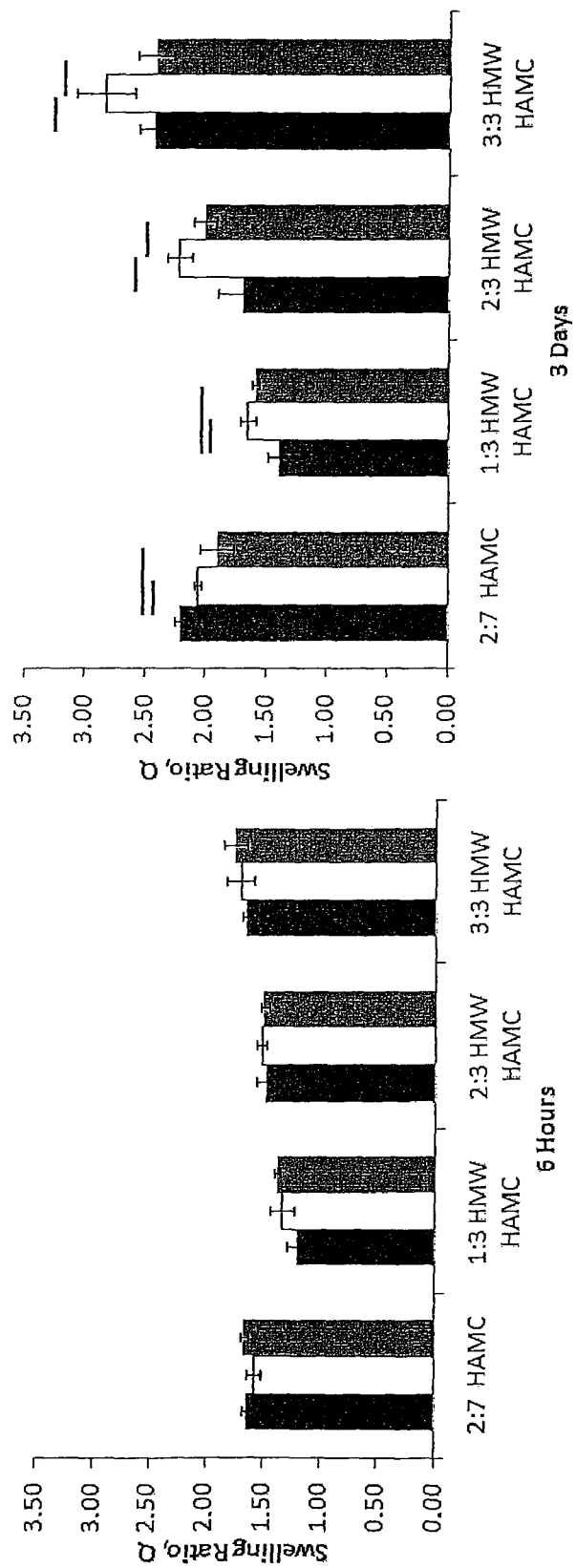
FIG. 2 illustrates swelling of hydrogel composites over time. The traces are: 0 mg/mL (■), 25 mg/mL (□), and 75 mg/mL (▩) of 220 nm polystyrene particles dispersed in the hydrogel. Specifically, equilibrium swelling of 1:3 and 2:3 HMW HAMC and their composites and composite 2:7 HAMC is similar to or less than 2:7 HAMC alone, suggesting that these formulations can be used in confined volumes such as the intrathecal space, in the same manner as 2:7 HAMC.

As evidence of composite drug delivery the swelling behaviour of HAMC composites was determined at particle loads of 25 and 75 mg/mL, and particle diameters of 220 and 830 nm. Polystyrene (PS) particles were used as model hydrophobic polymer beads to simulate PLGA microspheres because of their narrow size distribution and range of available diameters. No difference in swelling was observed as a function of particle diameter for any HAMC formulation at any loading (data not shown). As shown in FIG. 2 for 220 nm particles dispersed in various HAMC hydrogels, these formulations with nanoparticles reached maximum swelling on day 3, at which time an effect of particle loading on swelling became significant.

The swelling behaviour of the composites can be partially explained if the particles are considered as non-interacting spheres which increase the volume fraction of polymer, $v_{2,s}$, in the gel by displacing aCSF. According to the Peppas-Merrill equation of hydrogel swelling, Q decreases as $v_{2,s}$ is increased [Peppas, N. A. and E. W. Merrill, *Polyvinyl-Alcohol) Hydrogels-Reinforcement of Radiation-Crosslinked Networks by Crystallization*. Journal of Polymer Science Part a-Polymer Chemistry, 1976. 14(2): p. 441-457]. For example, a 75 mg/mL particle load increases the aqueous MC content in HMW HAMC from 3.0% to 3.2% by displacing aCSF. This mechanism accounts for the reduced swelling in HMW HAMC when particle loading was increased from 25 to 75 mg/mL for all blends, and why Q is independent of particle diameter, since only the total mass of buffer displaced is considered. It does not, however, account for the increase in Q from zero to 25 mg/mL particles in each HMW HAMC. This unexpected increase in swelling may be a kinetic effect not well described by equilibrium swelling theory. Importantly, both 1:3 and 2:3 HMW HAMC at 25 and 75 mg/mL swelled similarly to, or less than, the pre-existing drug delivery system, supporting the safety of these materials in vivo.

The graphs in FIG. 2 show that each of the HMW HAMC formulations swell similarly or less than 2:7 HAMC after six hours. All materials reached a maximum swelling ratio at 3 days. The traces are: 0 mg/mL (■), 25 mg/mL (□), and 75 mg/mL (▩) of 220 nm polystyrene particles dispersed in the hydrogel.

The in vitro degradation of the three HMW HAMC blends with and without PS particles was followed by measuring the swelling ratio over time relative to $Q_{max}$. For the HMW HAMC swelling traces in FIG. 3, 1:3 HMW HAMC was most stable, followed by 2:3 and 3:3 HMW HAMC. Since HAMC gels through physical cross-links between methylcellulose, the higher concentration of MC in the minimally swollen gels results in slower degradation. This is supported by Peppas and Merrill who showed that lower swelling ratios are the result of more physical cross-links and are therefore predictive of slower degradation/dissolution [Peppas, N. A. and E. W. Merrill, *Polyvinyl-Alcohol) Hydrogels—Reinforcement of Radiation-Crosslinked Networks by Crystallization*. Journal of Polymer Science Part a-Polymer Chemistry, 1976. 14(2): p. 441-457].

Dispersing nanoparticles in all HMW HAMC resulted in significantly slower degradation regardless of particle loading (25 or 75 mg/mL) or diameter (220 or 830 nm). For 1:3 HMW HAMC, inclusion of nanoparticles resulted in gels that retained 80% of $Q_{max}$ at 28 days relative to gels alone that retained only 60% of $Q_{max}$. For 2:3 and 3:3 HMW HAMC, dispersing hydrophobic nanoparticles stabilized the gel and left a majority of the composite intact when the blank hydrogels had completely degraded. For 2:3 HMW HAMC, which had degraded completely by 28 days, inclusion of nanoparticle resulted in 70-80% retention of $Q_{max}$. For 3:3 HMW HAMC, which had completely degraded at 21 days, the inclusion of particles resulted in 60-80% retention of $Q_{max}$ then, and 30-60% at 28 days. As with initial swelling, particle diameter did not measurably affect degradation. Based on previously observed differences between HAMC degradation in vitro and in vivo, where 2:7 HAMC was observed to degrade faster after intrathecal injection [C. E. Kang, et al., *A new paradigm for local and sustained release of therapeutic molecules to the injured spinal cord for neuroprotection and tissue repair*, TissueEng Part A 15 (3) (2009) 595-604.], it was desirable that the new drug delivery platform remain substantially intact at 28 days in vitro. 1:3 HMW HAMC met this criterion under all conditions and 2:3 HMW HAMC was satisfactory in the presence of nanoparticles.

Figure 4:
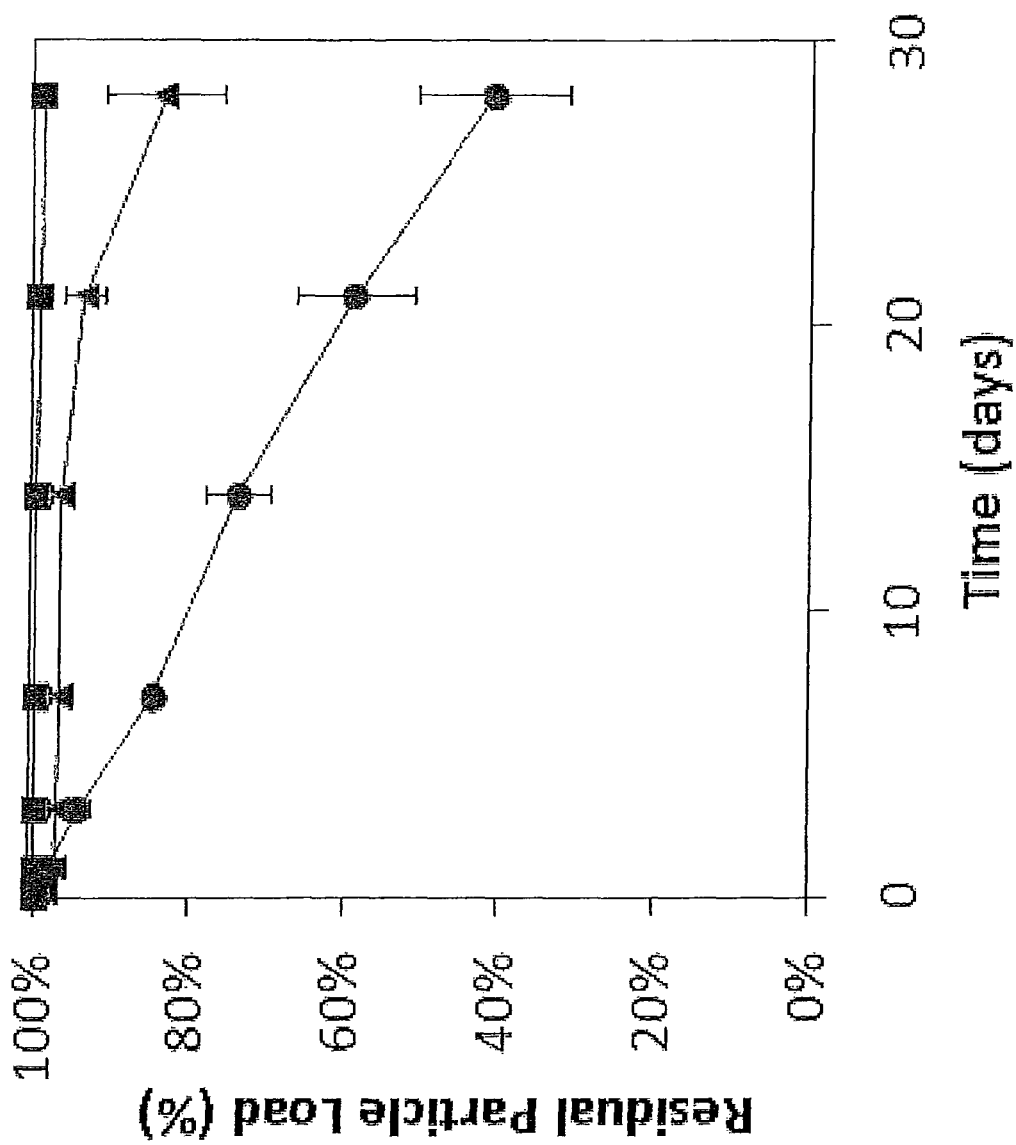
FIG. 4 illustrates residual particle load over time for a number of hydrogel composites. The traces are: 1:3 HMW HAMC (■), 2:3 HMW HAMC (▲), 3:3 HMW HAMC (●), each loaded with 25 mg/mL of 220 nm PS particles. Particles embedded in composite HAMC remain within composite HAMC until the composite begins to degrade: that is, they are not prematurely lost from the injectable composite until the normalized swollen volume falls below about 80%.

The residual particle load was quantified for the 220 nm particle loaded composites as a direct measure of the composite's utility as a drug delivery platform. The residual particle load, defined as the mass of particles in the gel at time, t, divided by the initial particle mass, was followed by injecting 150 mg of nanoparticle loaded hydrogel in 800 μL, of aCSF. Substantial numbers of the 220 nm and larger particles were not predicted to diffuse from the composite in the absence of HMW HAMC degradation because the particles were significantly larger than the mesh sizes typically reported for hydrogels [Lin, C. C. and A. T. Metters, *Hydrogels in controlled release formulations: network design and mathematical modeling*. Adv Drug Deliv Rev, 2006. 58(12-13): p. 1379-408]. In FIG. 4, a small release of less than 2% of nanoparticles was seen from each of the composites in the hours after injection, followed by a delay in particle loss as the composites shrunk with the reorganization of the MC hydrophobic network and formation of optimized cross-links [Schupper, N., Y. Rabin, and M. Rosenbluh, *Multiple stages in the aging of a physical polymer gel*. Macromolecules, 2008. 41(11): p. 3983-3994]. At 28 days the residual particle load was 40% for 3:3 HMW HAMC, 84% for 2:3 HMW HAMC and 98% for 1:3 HMW HAMC, following the degradation pattern of the hydrogels. Residual particle loads were not dependent on initial mass loading (25 or 75 mg/mL) after 28 days. These results were consistent with the characterization of 1:3 HMW HAMC as having the lowest swelling ratio, greatest stability, highest weight fraction of MC, and lowest predicted molecular weight between cross-links.

The mechanism of nanoparticle-mediated stabilization remains unclear, although one possibility is based on network optimization [Schupper, N., Y. Rabin, and M. Rosenbluh, *Multiple stages in the aging of a physical polymer gel*. Macromolecules, 2008. 41(11): p. 3983-3994], supported by the reduction in normalized swelling without loss of embedded particles in 1:3 HMW HAMC over 28 days and 2:3 HMW HAMC over 14 days. Considering dynamic association of MC chains, those near the surface of the gel have fewer neighbouring hydrophobic regions and are likely lost from the gel by diffusion. Dispersed hydrophobic particles may slow this process by associating with MC [Saunders, F. L., *Adsorption of Methylcellulose on Polystyrene Latexes*. Journal of Colloid and Interface Science, 1968. 28(3-4): p. 475], slowing diffusion and resulting in a higher fraction of MC chains re-forming hydrophobic junctions and stabilizing the composite.

Figure 3:
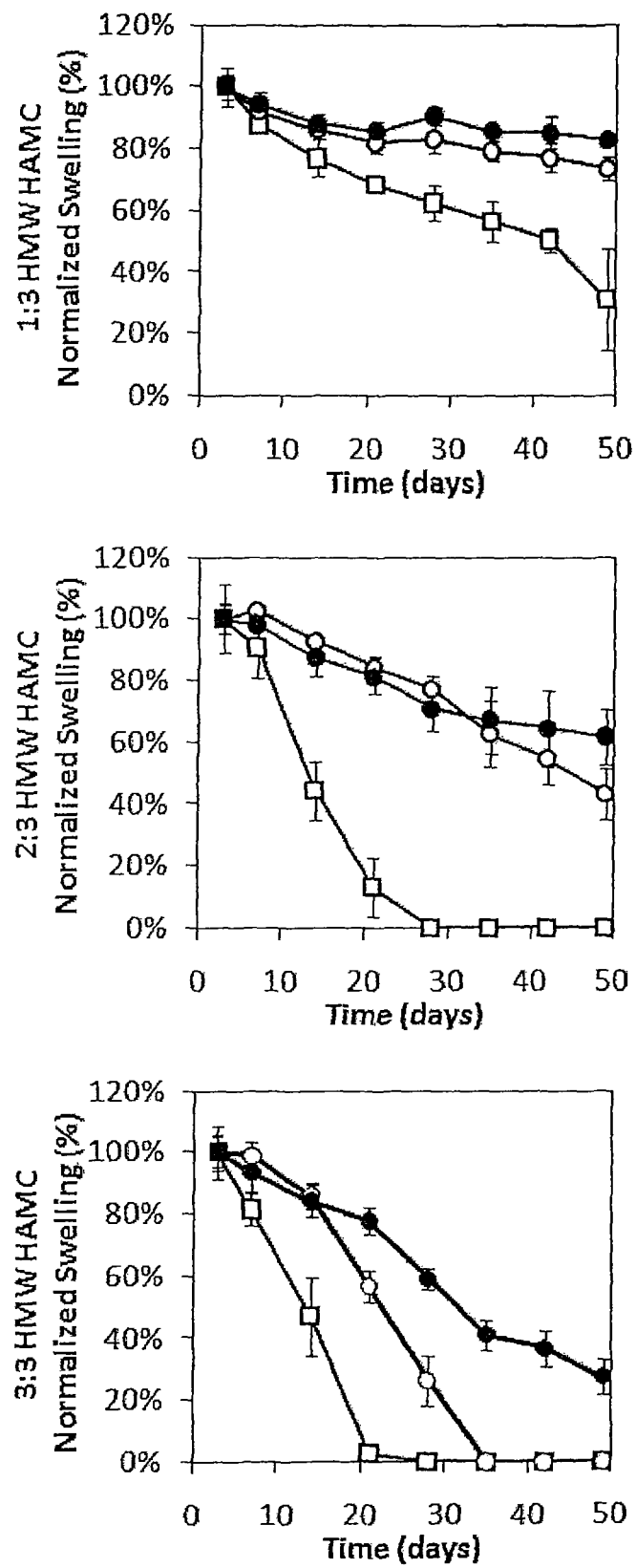
FIG. 3 illustrates utilizes normalized swelling as a proxy for mass loss and a measure of stability. In other experiments (data not shown) mass loss from the composite does not occur until normalized swollen volume falls below 80%.

FIG. 3 illustrates the degradation of HMW HAMC and composite HMW HAMC quantified by the swelling ratio and represented a change in composite volume relative to $Q_{max}$. Degradation of HMW HAMC (□) was faster than composite HMW HAMC of the same formulation in all cases. No significant effect of particle diameter on degradation was found. Open circles are 25 mg/mL of 220 nm particles (○), and filled circles are 75 mg/mL.

Figure 5:
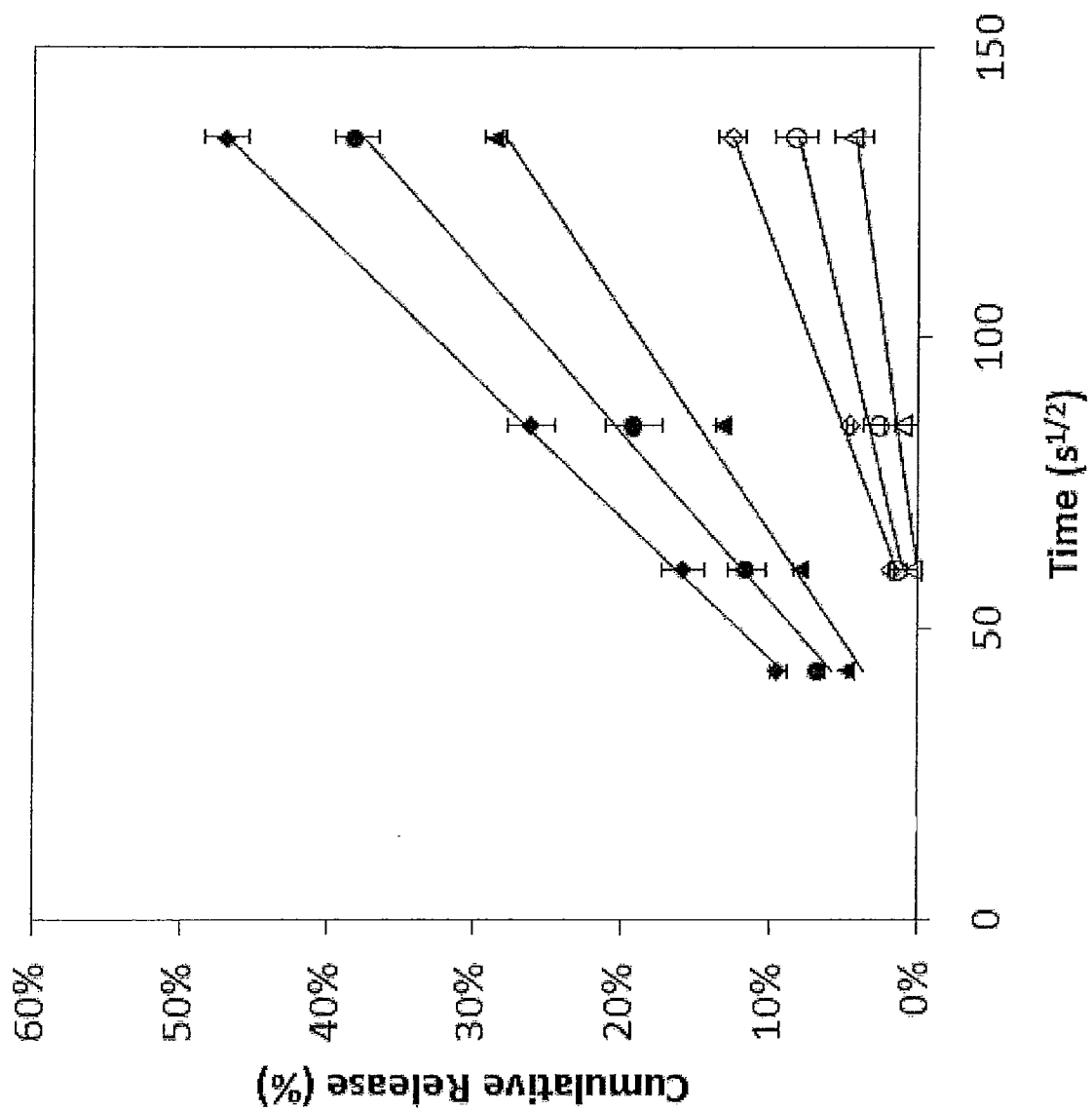
FIG. 5 illustrates the cumulative therapeutic agent release from a number of hydrogel composites. The traces are: 1:3 HMW HAMC (◇), 2:3 HMW HAMC (○), and 3:3 HMW HAMC (Δ). α-Chymotrypsin release is represented by filled symbols and IgG release by open symbols. When a protein is dispersed in soluble form within the hydrogel or composite it is released in a primarily Fickian fashion, being linear with $t^{1/2}$. The use of chymotrypsin and IgG illustrates this property is conserved across a wide range of molecular weights.

FIG. 5 illustrates the loss of particles from composite HMW HAMC as a strong function of gel composition. The traces are: 1:3 HMW HAMC (■), 2:3 HMW HAMC (▲), 3:3 HMW HAMC (●), each loaded with 25 mg/mL of 220 nm PS particles.

To study the possible effect of embedded particles on the mechanical properties of HMW HAMC the injectability of composite HMW HAMC through a 30 G needle from a Hamilton 250 μL glass syringe was tested. Surfactant free suspensions of low polydispersity PS particles ranging from 60 nm to 15.5 μm in diameter were lyophilized, added dry to each of the hydrogels up to 150 mg/mL, and mechanically dispersed. Given the inherent stiffness of HMW HAMC and the reported difficulty in evenly suspending hydrophobic particles in hydrogels [Liu, X., K. Nakamura, and A. M. Lowman, *Composite hydrogels for sustained release of therapeutic agents*. Soft Materials, 2003. 1(3): p. 393-408; Mackay, M. E., et al., *General strategies for nanoparticle dispersion*. Science, 2006. 311(5768): p. 1740-3], large diameter and higher weight percent formulations were expected not to be injectable due to incomplete dispersion and occlusion of the needle by particle aggregates. Surprisingly, each formulation was injectable at room temperature. The injection of higher concentrations and larger diameter particles enhances the utility of the drug delivery platform by both increasing the deliverable drug load and capturing the distinct release profiles reported for PLGA particles of different diameters [Sinha, V. R. and A. Trehan, *Biodegradable microspheres for protein delivery*. Journal of Controlled Release, 2003. 90(3): p. 261-280; Soppimath, K. S., et al., *Biodegradable polymeric nanoparticles as drug delivery devices*. J Control Release, 2001. 70(1-2): p. 1-20.].

Drug Diffusivity in Hydrogels

Next examined were the diffusion of two high molecular weight proteins, IgG (150 kg/mol) and α-chymotrypsin (25 kg/mol), from HMW HAMC since they were most likely to be restricted by sieving effects [Hennink, W. E., et al., *Controlled release of proteins from dextran hydrogels*. Journal of Controlled Release, 1996. 39(1): p. 47-55]. It was desirable that the normalized diffusion coefficient, $D/D_o$, be sufficiently large that the rate-limiting step in release of particle encapsulated drugs was not diffusion through the gel. In this manner long-term drug release is controlled by the particle formulation and the release profile is decoupled from molecular diffusivity. Plotting the fractional release of IgG and α-chymotrypsin against $t^{1/2}$ yielded a linear relationship, as predicted for Fickian diffusion [Ritger, P. L. and N. A. Peppas, *A Simple Equation for Description of Solute Release 1. Fickian and Non-Fickian Release from Non-Swellable Devices in the Form of Slabs, Spheres, Cylinders or Discs*. Journal of Controlled Release, 1987. 5: p. 23-36]. Applying a $D_o$ of $6.4 \times 10^{-7}$ cm²/s for IgG [Cruise, G. M., D. S. Scharp, and J. A. Hubbell, *Characterization of permeability and network structure of interfacially photopolymerized poly(ethylene glycol) diacrylate hydrogels*. Biomaterials, 1998. 19(14): p. 1287-94] and an estimated $D_o$ of $1.5 \times 10^{-6}$ cm²/s for α-chymotrypsin [Han, J. H., et al., *Lactitol-based poly(ether polyol) hydrogels for controlled release chemical and drug delivery systems*. Journal of Agricultural and Food Chemistry, 2000. 48(11): p. 5278-5282], the normalized diffusion coefficient of IgG ranged from 0.04 in 3:3 HMW HAMC to 0.25 in 1:3 HMW HAMC and α-chymotrypsin ranged from ~0.3 to ~0.8 in the same materials. It is clear from the non-zero intercept in FIG. 5 that swelling impacted drug release at these early times as penetration of aCSF into the gel retards drug release. This result was expected given that for all gels within 3 hours Q for all gels exceeded 1.25, the ratio above which swelling is a significant factor in drug release [Ritger, P. L. and N. A. Peppas, *A Simple Equation for Description of Solute Release 2. Fickian and Anomalous Release from Swellable Devices*. Journal of Controlled Release, 1987. 5: p. 37-42] and reduced the calculated value of D. The in vitro estimation of D is therefore smaller than what can be expected in vivo where the restrictive environment may prevent the gel from swelling more than 1.25× normal to the spinal cord. Both IgG and α-chymotrypsin diffuse from HMW HAMC relatively quickly and release is predicted to be complete within 24 hours based on the planar geometry of the gels after injection in vivo. This rate is advantageous, being slow enough to allow prolonged release of dissolved molecules yet fast enough that release of PLGA encapsulated molecules is not diffusion limited.

FIG. 4 illustrates that the slope of IgG and α-chymotrypsin release from HMW HAMC decreases as HA concentration increases, indicating HA slowed diffusion. $D/D_o$ was lowest for both molecules in 3:3 HMW HAMC, on the order of 0.3 and 0.04 for α-chymotrypsin and IgG, respectively. The non-zero intercept indicates that swelling has slowed drug release, reducing D. The traces are: 1:3 HMW HAMC (◇), 2:3 HMW HAMC (○), and 3:3 HMW HAMC (Δ). α-Chymotrypsin release is represented by filled symbols and IgG release by open symbols.

Drug Release from Composite Hydrogels

Figure 6:
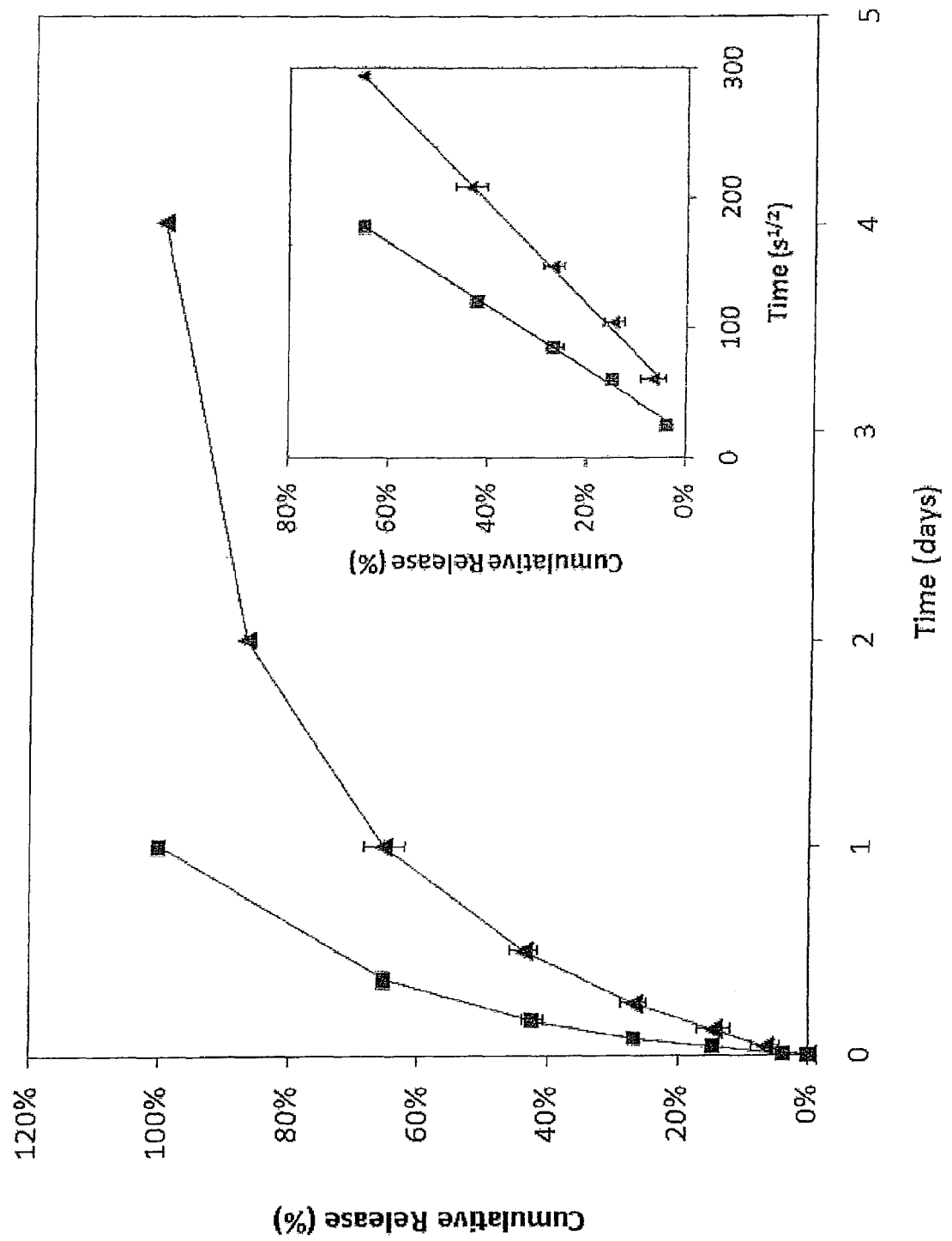
FIG. 6 illustrates the in vitro release of dissolved NBQX (■) and FGF-2 (▲) from 2:3 HMW HAMC. The release of the therapeutic molecules NBQX and FGF-2 from the gel is also Fickian.

After establishing that both 1:3 and 2:3 HMW HAMC composites met the in vitro design criteria, the release of six therapeutic molecules from 2:3 HMW HAMC was assessed. These were chosen because the HA content matched 2:7 HAMC and is thought to be an important component in HAMC's anti-inflammatory action. NBQX and FGF-2 have been shown to play a role in neuroprotection and thus fast release from the hydrogel is desirable. Both molecules were released in a diffusion-limited manner from 2:3 HMW HAMC, shown in the inset of FIG. 5, with a normalized diffusion coefficient on the order of 0.1. The release profiles, also plotted versus linear time in FIG. 5 for ease of comparison to particle mediated release in FIG. 6, show that NBQX is released from the hydrogel faster that FGF-2. The diffusive release in vitro is likely slower than that in vivo, where the release rate is bounded by fast unidirectional diffusion from a thin film [Crank, J., *The Mathematics of Diffusion*. 1956, Oxford: Clarendon Press] and the slow diffusion of many molecules through tissue [Kang, C. E., et al., *A New Paradigm for Local and Sustained Release of Therapeutic Molecules to the Injured Spinal Cord for Neuroprotection and Tissue Repair*. Tissue Eng Part A, 2008, Jimenez Hamann, M. C., C. H. Tator, and M. S. Shoichet, *Injectable intrathecal delivery system for localized administration of EGF and FGF-2 to the injured rat spinal cord*. Exp Neurol, 2005. 194(1): p. 106-19, Krewson, C. E., M. L. Klarman, and W. M. Saltzman, *Distribution of nerve growth factor following direct delivery to brain interstitium*. Brain Res, 1995. 680(1-2): p. 196-206].

Four neuroregenerative molecules (or models thereof) were encapsulated in formulations of PLGA particles and individually dispersed in 2:3 HMW HAMC for long term release. Encapsulation in PLGA particles is widely used to control temporal drug release. In these systems the release profile results from drug diffusion through pores in the hydrogel composite formed by dissolution of entrapped protein and degradation of PLGA. The data for the encapsulation of dbcAMP, EGF, α-chymotrypsin, and IgG are summarized in Table 2 and the drug release profiles from free particles are reported in FIG. 7.

FIG. 6 illustrates the in vitro release of dissolved NBQX (■) and FGF-2 (▲) from 2:3 HMW HAMC is diffusion limited (inset) and complete within 1 and 4 days, respectively (main graph). Fractional release normalized to the total initial drug mass for NBQX and to total detectable protein for FGF-2.

TABLE 2

Synthesis of drug loaded PLGA particles

| Molecule | Molecular Weight (kg/mol) | Encapsulation Efficiency (%) | Drug Loading (µg/mg) | Particle Yield (%) | Particle Size (µm) |
|---|---|---|---|---|---|
| dbcAMP | 0.469 | 51 | 68 | 50 | 37 ± 14 |
| EGF | 6.2 | 36 | 4.8 | 63 | 10 ± 2 |
| α-Chymotrypsin | 25 | 32 | 7 | 53 | 0.285, polydisperse |
| IgG | 150 | 56 | 14 | 61 | 0.272 ± 0.103 |

Figure 7:
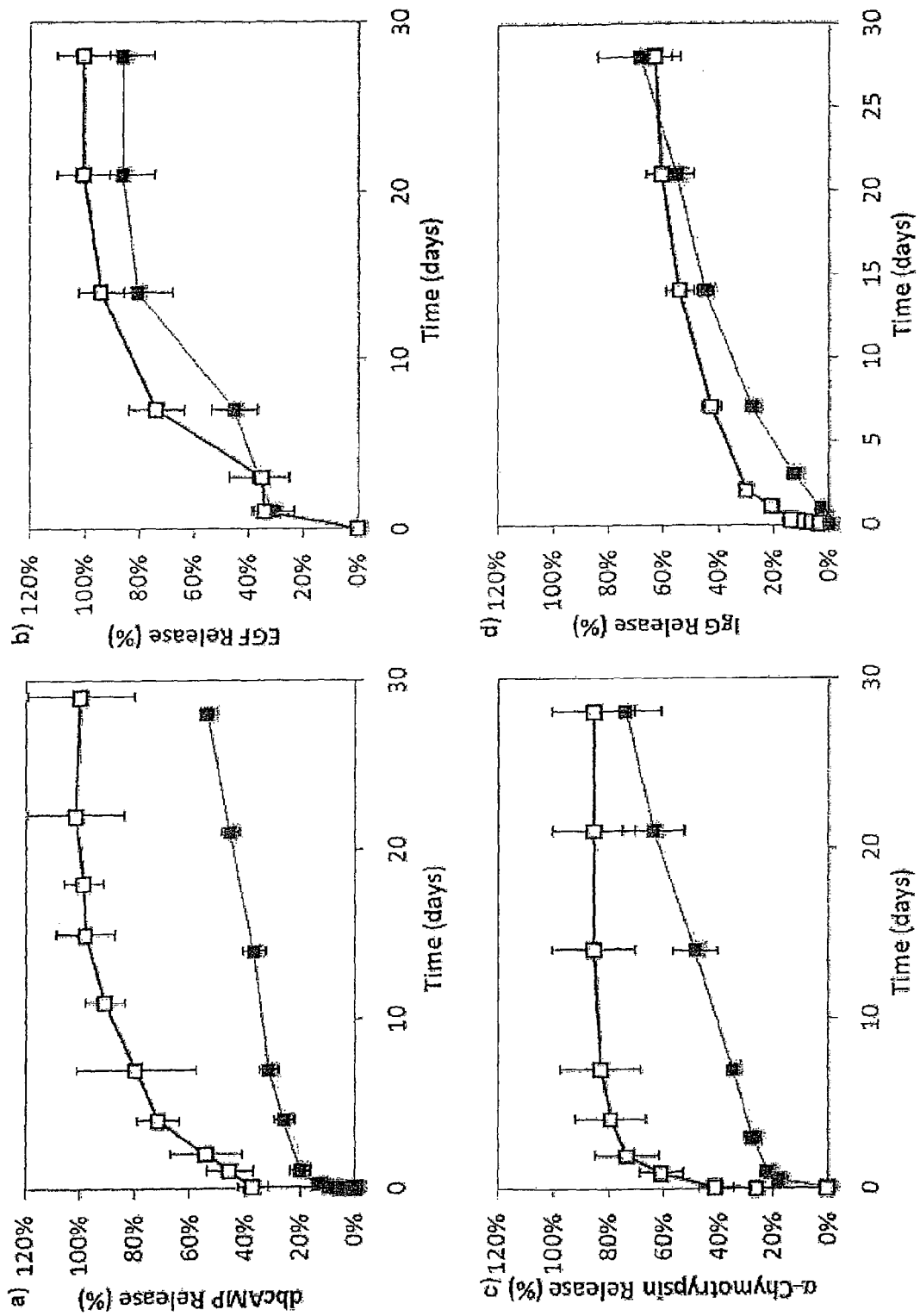
FIG. 7 illustrates cumulative release normalized to the amount of therapeutic agent encapsulated in particles. The open symbols indicate release from free particles for (a) dbcAMP, (b) EGF, (c) α-chymotrypsin, (d) IgG, and filled symbols from composite 2:3 HMW HAMC. Release of polymer micro or nanoparticle encapsulated drugs is unexpectedly slower and more linear when embedded in HMW HAMC that in aqueous suspension. The fast Fickian diffusion of dissolved drugs illustrated in FIGS. 5 and 6 indicates the sustained release is not the result of slow release through the hydrogel.

FIG. 7 illustrates the cumulative release normalized to the amount encapsulated in the particles. The open symbols indicate release from free particles for (a) dbcAMP, (b) EGF, (c) α-chymotrypsin, (d) IgG, and filled symbols from composite 2:3 HMW HAMC. The release of individual drugs from particles dispersed in 2:3 HMW HAMC is longer than from the corresponding particles alone.

As shown in FIG. 7, extended release over 28 days was achieved for these formulations. In a majority of these trials, the initial burst release characteristic of PLGA particles was reduced and subsequent release was typically more linear and longer from PLGA particles dispersed in HMW HAMC composite gels than from the particles alone. This observation was in agreement with the work of Ying et at [Ying, L., et al., *In vitro evaluation of lysozyme-loaded microspheres in thermosensitive methylcellulose-based hydrogel*. Chinese Journal of Chemical Engineering, 2007. 15(4): p. 566-572], although in the current case only a small portion of the effect was due to molecular diffusion through the gel. In HMW HAMC diffusion can only prolong release for 1-4 days after release from the particle, as reported in FIG. 5 for IgG and α-chymotrypsin and in FIG. 6 for NBQX and FGF-2. Visual observation of particle loaded composites, which remained opaque during these experiments, suggested decreased degradation of PLGA particles dispersed in HMW HAMC relative to particles dispersed in aqueous buffer. In each case the particles, which scatter light and cause the composite to appear opaque and white, remained intact. If the PLGA were hydrolyzed at the rate reported for free particles [Dunne, M., I. Corrigan, and Z. Ramtoola, *Influence of particle size and dissolution conditions on the degradation properties of polylactide-co-glycolide particles*. Biomaterials, 2000. 21(16): p. 1659-68], opacity would have decreased over time as particle size and number were reduced. If instead the rate of PLGA degradation was reduced in the composite, drug release would be slower than from particles alone and the composites would remain opaque as observed. This may be the result of MC adsorption onto the particle surface, resulting in slower diffusion of drug and degraded PLGA through pores in the hydrogel composite, mechanisms supported by the reduction in burst release observed for dbcAMP, α-chymotrypsin, and IgG. A MC/particle interaction is also supported by the increase in HMW HAMC stability on particle addition, discussed under the heading Hydrogel Swelling & Degradation. The atypical behaviour of the EGF loaded particles may indicate more of the drug was near the particle surface and less subject to variation in PLGA degradation.

As an injectable drug delivery platform, the particle-loaded hydrogels allow different drug formulations to be dispersed within the hydrogel to create a combination therapy while maintaining control of the resulting release profiles. Existing drug and particle formulations can be directly dispersed in the hydrogel without modification, and the combination of fast diffusion limited release from the dissolved phase and slow release of particle-borne drugs can be exploited such that release can be substantially decoupled from molecular weight. It has been demonstrated that the in vitro release of the small molecules NBQX and dbcAMP are over 1 and 28 days, respectively, and the release of proteins spanning 6-150 kg/mol over 4-28 days. Particle loads up to 15 wt % were injectable, resulting in a deliverable drug load of 1.1-10.1 mg per gram of composite as a function of PLGA particle properties. The 2:3 HMW HAMC used to evaluate drug release retained greater than 80% of the initial particle load after 28 days, suggesting that a high percentage of the drug loaded will be locally delivered at the site of injection.

This specific disclosure is directed toward a clinically acceptable drug delivery platform for the treatment of spinal cord injury. There are described a series of physical hydrogels composed of hyaluronan and methylcellulose which meet the design criteria of injectability, safe swelling, satisfactory diffusivity of molecules up to 150 kg/mol, high residual particle load, and significantly slower in vitro degradation relative to earlier reports. The slow degradation rate of HMW HAMC with particles dispersed therein suggests this as a platform for 28 day combination drug therapy. Composites with particle loads up to 15 wt % and 0.06-15.5 µm diameter remained injectable for all blends and that greater than 95% of the initial particle load was retained after 28 days in vitro in 1:3 HMW HAMC. Utilizing a combination of diffusion limited and particle mediated drug delivery, release of six neuroprotective and neuroregenerative drugs from 1 to 28 days was shown.

Method of Medical Treatment

In spinal cord injury, small blood vessels are ruptured and lead to hemorrhage and edema in the tissue parenchyma [I. Koyanagi, C. H. Tator, and P. J. Lea, *Three-dimensional analysis of the vascular system in the rat spinal cord with scanning electron microscopy of vascular corrosion casts. Part* 1: *Normal spinal cord*, Neurosurgery. 33 (1993) 277-83; discussion 283-4; I. Koyanagi, C. H. Tator, and P. J. Lea, *Three-dimensional analysis of the vascular system in the rat spinal cord with scanning electron microscopy of vascular corrosion casts. Part* 2: *Acute spinal cord injury*, Neurosurgery. 33 (1993) 285-91; discussion 292]. Reduced blood flow leads to widespread ischemia, ultimately contributing to tissue degeneration in a large area surrounding the initial injury. To induce blood vessel growth in tissue and thus reduce the ischemic impact, the angiogenic protein fibroblast growth factor 2 (FGF2) [R. Montesano, J. D. Vassalli, A. Baird, R. Guillemin, and L. Orci, *Basic fibroblast growth factor induces angiogenesis in vitro*, Proc Natl Acad Sci USA. 83 (1986) 7297-301; Y. Shing, J. Folkman, C. Haudenschild, D. Lund, R. Crum, and M. Klagsbrun, *Angiogenesis is stimulated by a tumor-derived endothelial cell growth factor*, Journal of Cellular Biochemistry. 29 (1985) 275-87; M. Relf, S. LeJeune, P. A. Scott, S. Fox, K. Smith, R. Leek, A. Moghaddam, R. Whitehouse, R. Bicknell, and A. L. Harris, *Expression of the angiogenic factors vascular endothelial cell growth factor, acidic and basic fibroblast growth factor, tumor growth factor beta-*1, *platelet-derived endothelial cell growth factor, placenta growth factor, and pleiotrophin in human primary breast cancer and its relation to angiogenesis*, Cancer Res. 57 (1997) 963-9] was delivered with composite HAMC into the intrathecal space.

Physical hydrogel blends of hyaluronan (HA) and methyl cellulose (MC) were prepared in aCSF at 1 wt % 2600 kg/mol HA and 3 wt % 300 kg/mol MC as previously reported (1:3 HMW HAMC [M. D. Baumann, C. E. Kang, J. C. Stanwick, Y. Wang, H. Kim, Y. Lapitsky, and M. S. Shoichet, *An injectable drug delivery platform for sustained combination therapy*, J Control Release. (2009)]. Briefly, MC and HA were sequentially mechanically dispersed in aCSF and allowed to dissolve at 4° C. To form composite 1:3 HMW HAMC, slurries of particles were added together for a final concentration of 100 mg/mL. PLGA nanoparticles were prepared from a w/o/w double emulsion as previously described [Li, Y., et al., *Effects of the AMPA receptor antagonist NBQX on the development and expression of behavioral sensitization to cocaine and amphetamine*. Psychopharmacology (Berl), 1997. 134(3): p. 266-76], either as blank nanoparticles or encapsulating FGF2.

Figure 8:
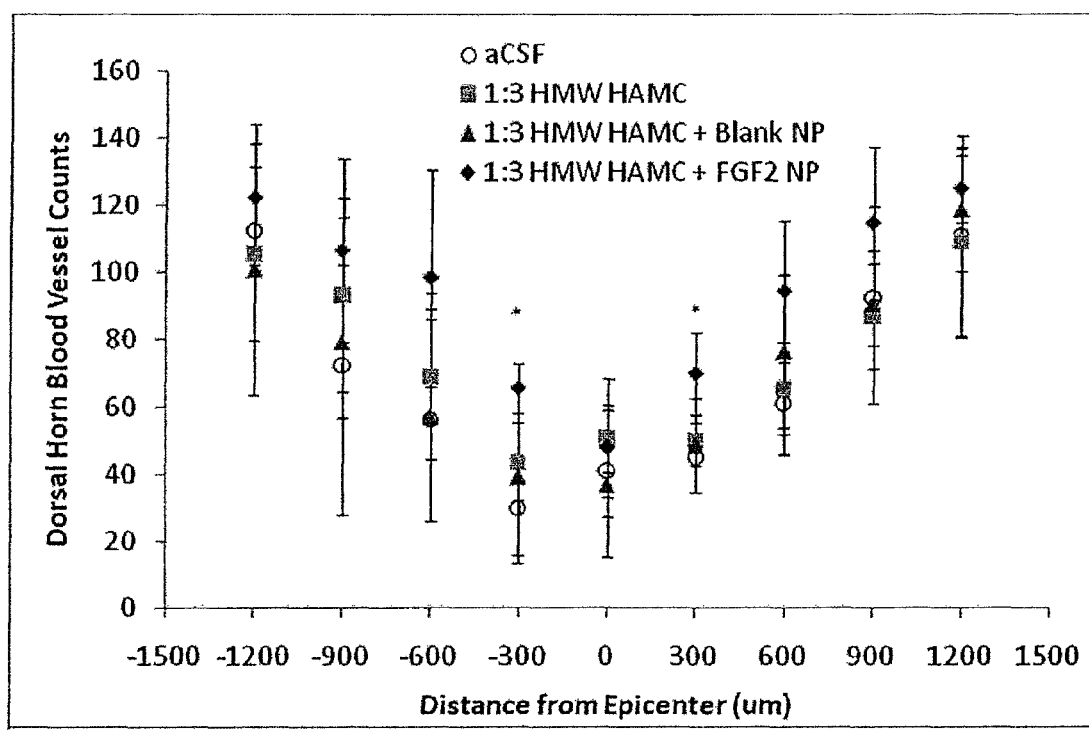
FIG. 8 is a graphical representation of dorsal horn blood vessel counts versus distance from epicenter.

All animal procedures were performed in accordance with the Guide to the Care and Use of Experimental Animals (Canadian Council on Animal Care) and protocols were approved by the Animal Care Committee of the Research Institute of the University Health Network. Sprague Dawley rats were anaesthetized by inhalation of halothane and a laminectomy was performed at the T1-T2 vertebral level. All animals sustained a moderate compressive spinal cord injury at T2 using a modified aneurysm clip calibrated to a closing force of 26 g for 60 s, as previously described [A. S. Rivlin and C. H. Tator, *Effect of duration of acute spinal cord compression in a new acute cord injury model in the rat*, Surg Neurol. 10 (1978) 38-43]. After a laminectomy, the dura was punctured with a bevelled 30 G needle at T2, and a 30 G blunt-tipped needle was inserted into the intrathecal space. Each animal received 10 µl of either: 1) artificial cerebrospinal fluid (aCSF), 2) HMW HAMC, 3) composite HAMC, or 4) composite HAMC loaded with FGF2 pre-heated to 37° C. Following injection, the overlying muscles and fascia were sutured closed and the rats were ventilated with pure oxygen and placed under a heat lamp for recovery. Buprenorphine was administered every 12 h for 3 days post-surgery for pain management. The animals were sacrificed 28 days after surgery and perfused intracardially with 4% paraformaldehyde under terminal anaesthesia with sodium pentobarbital. A 20 mm segment of spinal cord encompassing the injury site was harvested from each animal, dehydrated in 30% sucrose, and stored at −80° C. until cryoprocessing. Cords were then cut cross-sectionally into 20 um sections and every third section rostrocaudally from the epicenter stained with SMI-71, a marker for mature blood vessels. Blood vessels were then counted in the dorsal horns of the spinal cord (See FIG. 8). Statistical significance was determined by ANOVA followed by Tukey's post-hoc test.

Results for Localized and Sustained Delivery FGF2 with Composite HAMC

Following a moderate spinal cord injury, FGF2 was delivered from composite HAMC on the dorsal surface of the injured spinal cord. FGF2 promotes endothelial cell proliferation, which leads to blood vessel formation [C. Basilico and D. Moscatelli, *The FGF family of growth factors and oncogenes*, Adv Cancer Res. 59 (1992) 115-65; A. Bikfalvi, S. Klein, G. Pintucci, and D. B. Rifkin, *Biological roles of fibroblast growth factor-*2, Endocr Rev. 18 (1997) 26-45]. Mature blood vessels counted in the dorsal horns of the injured spinal cord showed that FGF2 delivery with composite HAMC results in angiogenesis. Angiogenesis can reduce the ischemic injury in tissue.

Thus it has been demonstrated that sustained delivery of FGF2 with the composite HAMC provides enhanced blood vessels in the dorsal horns after spinal cord injury. FGF2 is an angiogenic molecule, and can be substituted with FGF1, vascular endothelial growth factor (VEGF), or platelet derived growth factor (PDGF) to induce angiogenesis in tissue.

The disclosures of all publications, patent applications and patents referenced herein are incorporated herein by reference in their entireties.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What we claim is:

1. A hydrogel composite comprising:
a hydrogel comprising a blend of a solution containing dissolved methylcellulose and a hyaluronan wherein the hyaluronan and the methylcellulose are present in a weight ratio of hyaluronan to methylcellulose in an amount of about 2:3; and dispersed hydrophobic polymeric particles selected from microparticles, being a particle size of 1 micron to 30 microns and nanoparticles being a particle size of from 10 nm to 1000 nm, wherein some or all of which hydrophobic polymeric microparticles and nanoparticles encapsulate at least one therapeutic agent and wherein the dispersed hydrophobic polymeric particles interact with the hydrogel through hydrophobic interactions between the hydrogel and the dispersed hydrophobic polymeric particles to alter the release of the at least one therapeutic agent, and wherein the stability of the hydrogel composite with the dispersed hydrophobic polymeric particles is enhanced relative to the stability of the hydrogel alone, and each of the at least one therapeutic agent has a sustained release profile that extends for about 28 days or more.

2. The hydrogel composite as claimed in claim 1, wherein release of the at least one therapeutic agent is not dependent on gel formulation.

3. The hydrogel composite as claimed in claim 1, wherein the hydrophobic polymer particles are selected from degradable and non-degradable hydrophobic polymers chosen from the group consisting of: aliphatic polyesters; polydioxanones; polyhydroxyalkanoate; polyanhydrides; aliphatic-aromatic polyesters; aliphatic polyamides; amide ester copolymers; urethane ester copolymers; urethane amide copolymers and urea ester copolymers; polyacrylates; ethylene-vinyl acetates; acyl substituted cellulose acetates; non-degradable polyurethanes; polystyrenes; polyvinyl chlorides; polyvinyl fluorides; poly(vinyl imidazoles); chlorosulphonate polyolefins; polyethylene oxides; starches; and blends or copolymers thereof; and
wherein the hydrogel comprises a blend of a solution containing dissolved methylcellulose and a solution containing dissolved hyaluronan.

4. The hydrogel composite as claimed in claim 1, wherein the dispersed hydrophobic polymeric particles comprise a particle load of from about 1 to about 20 wt %, based on the composite.

5. The hydrogel composite as claimed in claim 1, wherein the dispersed hydrophobic polymeric particles are selected from particle sizes of form about 50 nm to about 40 µm; and wherein the at least one therapeutic agent has a sustained, substantially liner release profile that extends for about 28 days or more.

6. The hydrogel composite as claimed in claim 1, wherein the therapeutic agent is encapsulated in the dispersed hydrophobic polymeric particles in an amount in the range of from about 0.1 to about 30 wt % of particle mass;
wherein the hydrogel comprises a blend of a solution containing dissolved methylcellulose and a solution containing dissolved hyaluronan; and
wherein the at least one therapeutic agent has a sustained, substantially linear release profile that extends for about 28 days or more.

7. The hydrogel composite as claimed in claim 1, wherein the aqueous solution is an aqueous solution selected from the group comprising water, saline, artificial cerebrospinal fluid, and buffered solutions;
wherein the hydrogel comprises a blend of a solution containing dissolved methylcellulose and a solution containing dissolved hyaluronan; and
wherein the at least one therapeutic agent has a sustained, substantially linear release profile that extends for about 28 days or more.

8. The hydrogel composite as claimed in claim 1 having an altered chemical functionality by the addition of at least one functional group to the hyaluronan or the methylcellulose selected from non-ionic polymers selected from the group consisting of carboxymethylcellulose sodium, hydrophobically modified hydroxyethyl cellulose, hydroxypropyl cellulose, and mixtures thereof, the functional group being selected from the group consisting of carboxylic acid, primary amine, aldehyde, hydrazide, maleimide, thiol, furan, alkyne, azide, alkene, urethane, and primary alcohol.

9. The hydrogel composite as claimed in claim 1 wherein the therapeutic agent is selected from the group comprising: anaesthetics for use in caudal, epidural, inhalation, injectable, retrobulbar, and spinal applications; analgesics, selected from the group comprising: acetaminophen, ibuprofen, fluriprofen, ketoprofen, voltaren, phenacetin and salicylamide; anti-inflammatories selected from the group comprising: naproxen and indomethacin; antihistamines, selected from the group comprising: chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group comprising: dextromethorphan hydrobromide and guaifenesin; expectorants; decongestants, selected from the group comprising: phenylephrine hydrochloride, phenylpropanolamine hydrochloride, pseudoephedrine hydrochloride, and ephedrine; antibiotics selected from the group comprising: amebicides, broad and medium spectrum, fungal medications, monobactams and viral agents; bronchodilators selected from the group comprising: theophylline, albuterol and terbutaline; cardiovascular preparations selected from the group comprising: diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides; central nervous system drugs selected from the group comprising: thioridazine, diazepam, meclizine, ergoloid mesylates, chlorpromazine, carbidopa and levodopa; metal salts selected from the group comprising: potassium chloride and lithium carbonate; minerals selected from the group consisting of iron, chromium, molybdenum and potassium; immunomodulators; immunosuppressives selected from the group comprising: minocycline, cyclosporine A; thyroid preparations selected from the group comprising: synthetic thyroid hormone, and thyroxine sodium; peptide and glycoprotein hormones and analogues selected from the group comprising: human chorionic gonadotrophin (HCG), corticotrophin, human growth hormone (HGH-Somatotrophin) and erythropoietin (EPO); steroids and hormones selected from the group comprising: ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP; and others; vitamins selected from the group comprising: water-soluble vitamins and veterinary formulations; growth factors selected from the group comprising: EGF, FGF2 and neurotrophin; peptides, peptide mimetics and other protein preparations; DNA; and, small interfering RNAs; with or without a pharmaceutically acceptable carrier or preservative; and wherein the hydrogel composite has an altered rate of degradation by cross-linking the hyaluronan or by increasing the hydrophobicity of the hyaluronan.

10. A method for manufacturing a hydrogel composite as claimed in claim 1 which comprises the steps of 1) providing an aqueous solution of dissolved methylcellulose; 2) mixing hyaluronan into the aqueous solution, wherein the hyaluronan and the methylcellulose are present in a weight ratio of hyaluronan to methylcellulose in an amount of about 2:3; and 3) dispersing hydrophobic polymeric particles being a particle size of 1 micron to 30 microns and nanoparticles being in a particle size of from 10 nm to 1000 nm into the aqueous solution to form a stable hydrogel composite that has enhanced stability relative to a hydrogel without the dispersed hydrophobic polymer particles.

11. A method for promoting angiogenesis in a subject with spinal cord injury comprising delivering directly into a intrathecal or sub-dural space of said subject, a hydrogel composite of claim 1, to promote endothelial cell proliferation and blood vessel formation; wherein the therapeutic agent promotes angiogenesis.

12. The method as claimed in claim 11, comprising delivering directly into an intrathecal space of said subject, a hydrogel composite of claim 1, wherein the at least one therapeutic agent is selected from the group consisting of FGF2, FGF1, vascular endothelial growth factor (VEGF), platelet derived growth factor (PDGF), angiopoietins 1, and angiopoietin 2.

13. The hydrogel composite of claim 1, wherein the at least one therapeutic agent has a sustained, substantially linear release profile that extends for about 28 days or more.

* * * * *

UNITED STATES PATENT AND TRADEMARK OFFICE
CERTIFICATE OF CORRECTION

PATENT NO. : 9,205,046 B2
APPLICATION NO. : 12/778879
DATED : December 8, 2015
INVENTOR(S) : Shoichet et al.

It is certified that error appears in the above-identified patent and that said Letters Patent is hereby corrected as shown below:

In the specification,

\*Col. 1, line 13
After "entirety" insert -- . --

\*Col. 5, line 41
"derivatives" should be – derivative –

\*Col. 5, line 55
"derivatives" should be – derivative –

\*Col. 7, line 12
"hylaruonan" should be – hyaluronan –

\*Col. 7, line 30
"carbxoylate" should be – carboxylate –

\*Col. 7, line 35
Delete "bear"

\*Col. 8, line 40
"g/mol" should be – kg/mol –

\*Col. 8, line 44
"polypropylene" should be – poly(propylene –

\*Col. 9, line 61
"Localised" should be – Localized –

Signed and Sealed this
Tenth Day of May, 2016

Michelle K. Lee
*Director of the United States Patent and Trademark Office*

*Col. 10, line 66
"ethylene" should be – (ethylene –

*Col. 11, line 4
"poly(DL lactide" should be – poly(D,L-lactide –

*Col. 12, line 13
After "Publication" delete "."

*Col. 15, line 47
"(ie." should be – (i.e. –

*Col. 15, line 47
Delete "weeks" (2nd occurrence)

*Col. 15, line 58
"behaviour" should be – behavior –

*Col. 15, line 59
"are" should be – is –

*Col. 15, line 65
Delete "are" (2nd occurrence)

*Col. 16, line 9
"HAMC:" should be – HAMC; –

*Col. 16, line 10
Delete "utilizes"

*Col. 16, line 44
"that" should be – than –

*Col. 16, line 47
"hydrogel." should be – hydrogel; –

*Col. 17, line 23
"Calif." should be – CA –

*Col. 17, line 27
Delete "of"

*Col. 19, line 62
"Calif." should be – CA –

*Col. 21, line 11
"gels." should be – gels, –

*Col. 21, line 56
"behaviour" should be – behavior –

*Col. 22, line 1
"behaviour" should be – behavior –

*Col. 23, line 41
"neighbouring" should be – neighboring –

*Col. 25, line 43
"that" should be – than –

*Col. 26, line 67
"behaviour" should be – behavior –

*Col. 28, line 48
"um" should be – μm –

In the claims,

*Col. 29, claim 5, line 67
"form" should be – from –

*Col. 30, claim 5, line 2
"liner" should be – linear –

*Col. 30, claim 8, line 24
After "1" insert -- , --

*Col. 30, claim 9, line 34
After "1" insert -- , --

*Col. 30, claim 9, lines 39-40
After "anti-inflammatories" insert -- , --

*Col. 30, claim 9, lines 46-47
After "antitussives" insert -- , --

*Col. 30, claim 9, line 51
After "antibiotics" insert -- , --

CERTIFICATE OF CORRECTION (continued)
U.S. Pat. No. 9,205,046 B2

*Col. 30, claim 9, line 54
After "bronchodilators" insert -- , --

*Col. 30, claim 9, line 56
After "preparations" insert -- , --

*Col. 30, claim 9, line 62
After "drugs" insert -- , --

*Col. 30, claim 9, line 64
After "salts" insert -- , --

*Col. 30, claim 9, line 65
After "minerals" insert -- , --

*Col. 30, claim 9, line 67; Col. 31, line 1
After "immunosuppressives" insert -- , --

*Col. 31, claim 9, line 2
After "preparations" insert -- , --

*Col. 31, claim 9, line 4
After "analogues" insert -- , --

*Col. 31, claim 9, line 8
After "hormones" insert -- , --

*Col. 31, claim 9, line 15
";" should be – , –

*Col. 31, claim 9, line 15
After "vitamins" insert -- , --

*Col. 31, claim 9, line 17
After "factors" insert -- , --

*Col. 31, claim 9, line 20
";" should be – , –

*Col. 32, claim 11, line 11
"a" should be – an –